(12) United States Patent
Shrivastava

(10) Patent No.: US 12,285,182 B2
(45) Date of Patent: Apr. 29, 2025

(54) DEVICES AND METHODS FOR REMOVING AN EMBOLUS

(71) Applicant: INNOVA VASCULAR, INC., Irvine, CA (US)

(72) Inventor: Sanjay Shrivastava, Irvine, CA (US)

(73) Assignee: INNOVA VASCULAR, INC., Irvine, CA (US)

( * ) Notice: Subject to any disclaimer, the term of this patent is extended or adjusted under 35 U.S.C. 154(b) by 549 days.

(21) Appl. No.: 17/691,914

(22) Filed: Mar. 10, 2022

(65) Prior Publication Data

US 2022/0192690 A1  Jun. 23, 2022

Related U.S. Application Data

(63) Continuation-in-part of application No. 16/597,727, filed on Oct. 9, 2019, now Pat. No. 11,272,945.

(60) Provisional application No. 62/744,107, filed on Oct. 10, 2018.

(51) Int. Cl.
*A61B 17/221* (2006.01)

(52) U.S. Cl.
CPC .... *A61B 17/221* (2013.01); *A61B 2017/2215* (2013.01)

(58) Field of Classification Search
CPC ........ A61B 17/221; A61B 2017/00991; A61B 2017/2215; A61B 2090/0811; A61B 2090/3966
See application file for complete search history.

(56) References Cited

U.S. PATENT DOCUMENTS

| | | |
|---|---|---|
| 4,880,408 A | 11/1989 | Cumes et al. |
| 5,246,011 A | 9/1993 | Caillouette |
| 5,419,774 A | 5/1995 | Willard et al. |
| 5,429,616 A | 7/1995 | Schaffer |
| 5,476,450 A | 12/1995 | Ruggio |
| 5,938,645 A | 8/1999 | Gordon |
| 6,454,741 B1 | 9/2002 | Muni et al. |
| 6,481,439 B1 | 11/2002 | Lewis et al. |
| 6,508,782 B1 | 1/2003 | Evans et al. |
| 6,776,770 B1 | 8/2004 | Trerotola |
| 7,479,106 B2 | 1/2009 | Banik et al. |

(Continued)

FOREIGN PATENT DOCUMENTS

| | | |
|---|---|---|
| AU | 2021257925 A1 | 11/2021 |
| AU | 2021236459 B2 | 2/2024 |

(Continued)

OTHER PUBLICATIONS

Deak et al., "Rotational thrombectomy of acute peripheral vascular occlusions using the ThromCat XT device: techniques, indications and initial results", Diagnostic and Interventional Radiology, vol. 17, No. 3, Sep. 2011, Online Available at: https://doi.org/10.4261/1305-3825.DIR.3687-10.2, pp. 283-289.

(Continued)

*Primary Examiner* — Mohamed G Gabr
(74) *Attorney, Agent, or Firm* — NGUYEN TARBET IP Law

(57) ABSTRACT

A clot retrieval device is described herein. The clot retrieval device includes a capturing basket that is deployable to the side of a clot in a blood vessel. The capturing basket is configured to allow for the clot to ingress into the capturing basket and surround at least a portion of the clot.

20 Claims, 13 Drawing Sheets

(56) References Cited

U.S. PATENT DOCUMENTS

| | | |
|---|---|---|
| 7,686,825 B2 | 3/2010 | Hauser et al. |
| 7,901,426 B2 | 3/2011 | Gilson et al. |
| 7,942,852 B2 | 5/2011 | Mas et al. |
| 7,998,104 B2 | 8/2011 | Chang |
| 8,057,505 B2 | 11/2011 | Neilan et al. |
| 8,157,760 B2 | 4/2012 | Criado et al. |
| 8,252,020 B2 | 8/2012 | Hauser et al. |
| 8,382,817 B2 | 2/2013 | Pappas et al. |
| 8,439,963 B2 | 5/2013 | Dickinson et al. |
| 8,545,514 B2 | 10/2013 | Ferrera |
| 8,574,262 B2 | 11/2013 | Ferrera et al. |
| 8,585,713 B2 | 11/2013 | Ferrera et al. |
| 8,632,584 B2 | 1/2014 | Henkes et al. |
| 8,663,301 B2 | 3/2014 | Riina et al. |
| 8,679,142 B2 | 3/2014 | Slee et al. |
| 8,715,312 B2 | 5/2014 | Burke et al. |
| 8,728,141 B2 | 5/2014 | Riina et al. |
| 8,734,374 B2 | 5/2014 | Aklog et al. |
| 8,777,976 B2 | 7/2014 | Brady et al. |
| 8,784,434 B2 | 7/2014 | Rosenbluth et al. |
| 8,852,205 B2 | 10/2014 | Brady et al. |
| 8,915,950 B2 | 12/2014 | Cam et al. |
| 8,926,680 B2 | 1/2015 | Ferrera et al. |
| 8,926,681 B2 | 1/2015 | Levy et al. |
| 8,940,003 B2 | 1/2015 | Slee et al. |
| 8,945,143 B2 | 2/2015 | Ferrera et al. |
| 8,945,172 B2 | 2/2015 | Ferrera et al. |
| 8,956,386 B2 | 2/2015 | Hauser et al. |
| 8,956,475 B2 | 2/2015 | Riina et al. |
| 8,968,330 B2 | 3/2015 | Rosenbluth et al. |
| 8,968,382 B2 | 3/2015 | Riina et al. |
| 9,055,963 B2 | 6/2015 | Miloslavski et al. |
| 9,089,404 B2 | 7/2015 | Zaver et al. |
| 9,108,018 B2 | 8/2015 | Dickinson et al. |
| 9,114,001 B2 | 8/2015 | Losordo et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,204,887 B2 | 12/2015 | Cully et al. |
| 9,254,205 B2 | 2/2016 | Wainwright et al. |
| 9,259,237 B2 | 2/2016 | Quick et al. |
| 9,301,769 B2 | 4/2016 | Brady et al. |
| 9,301,831 B2 | 4/2016 | Kusleika et al. |
| 9,314,329 B2 | 4/2016 | Dickinson et al. |
| 9,320,532 B2 | 4/2016 | Ferrera et al. |
| 9,326,792 B2 | 5/2016 | Dickinson et al. |
| 9,351,749 B2 | 5/2016 | Brady et al. |
| 9,351,859 B2 | 5/2016 | Cam et al. |
| 9,387,098 B2 | 7/2016 | Ferrera et al. |
| 9,402,707 B2 | 8/2016 | Brady et al. |
| 9,408,620 B2 | 8/2016 | Rosenbluth et al. |
| 9,433,429 B2 | 9/2016 | Vale et al. |
| 9,439,664 B2 | 9/2016 | Sos |
| 9,445,829 B2 | 9/2016 | Brady et al. |
| 9,463,036 B2 | 10/2016 | Brady et al. |
| 9,468,442 B2 | 10/2016 | Huynh et al. |
| 9,468,739 B2 | 10/2016 | Sutherland et al. |
| 9,486,224 B2 | 11/2016 | Riina et al. |
| 9,486,608 B2 | 11/2016 | Sutherland et al. |
| 9,504,551 B2 | 11/2016 | Shrivastava et al. |
| 9,526,864 B2 | 12/2016 | Quick |
| 9,526,865 B2 | 12/2016 | Quick |
| 9,532,803 B2 | 1/2017 | Dickinson et al. |
| 9,539,022 B2 | 1/2017 | Bowman |
| 9,545,263 B2 | 1/2017 | Lenihan et al. |
| 9,597,171 B2 | 3/2017 | Shrivastava et al. |
| 9,610,180 B2 | 4/2017 | Cam et al. |
| 9,642,635 B2 | 5/2017 | Vale et al. |
| 9,642,639 B2 | 5/2017 | Brady et al. |
| 9,687,245 B2 | 6/2017 | Molaei et al. |
| 9,692,557 B2 | 6/2017 | Murphy |
| 9,700,332 B2 | 7/2017 | Marchand et al. |
| 9,706,998 B2 | 7/2017 | Dickinson et al. |
| 9,707,002 B2 | 7/2017 | Henkes et al. |
| 9,713,475 B2 | 7/2017 | Divino et al. |
| 9,717,519 B2 | 8/2017 | Rosenbluth et al. |
| 9,763,665 B2 | 9/2017 | Riina et al. |
| 9,782,201 B2 | 10/2017 | Dickinson et al. |
| 9,801,644 B2 | 10/2017 | Ulm, III |
| 9,833,253 B1 | 12/2017 | Ulm, III |
| 9,844,387 B2 | 12/2017 | Marchand et al. |
| 9,848,975 B2 | 12/2017 | Hauser |
| 9,907,643 B2 | 3/2018 | Kusleika et al. |
| 9,943,427 B2 | 4/2018 | Losordo et al. |
| 9,962,164 B2 | 5/2018 | Losordo et al. |
| 9,993,257 B2 | 6/2018 | Losordo et al. |
| 10,004,531 B2 | 6/2018 | Rosenbluth et al. |
| 10,016,211 B2 | 7/2018 | Ferrera et al. |
| 10,016,266 B2 | 7/2018 | Hauser |
| 10,034,680 B2 | 7/2018 | Brady et al. |
| 10,045,790 B2 | 8/2018 | Cox et al. |
| 10,070,878 B2 | 9/2018 | Ma |
| 10,080,575 B2 | 9/2018 | Brady et al. |
| 10,098,651 B2 | 10/2018 | Marchand et al. |
| 10,123,803 B2 | 11/2018 | Ferrera et al. |
| 10,123,804 B2 | 11/2018 | Cam et al. |
| 10,136,987 B2 | 11/2018 | Dickinson et al. |
| 10,201,360 B2 | 2/2019 | Vale et al. |
| 10,238,406 B2 | 3/2019 | Cox et al. |
| 10,265,085 B2 | 4/2019 | Zaidat |
| 10,265,086 B2 | 4/2019 | Vale et al. |
| 10,271,978 B2 | 4/2019 | Wainwright et al. |
| 10,278,717 B2 | 5/2019 | Brady et al. |
| 10,285,720 B2 | 5/2019 | Gilvarry et al. |
| 10,285,800 B2 | 5/2019 | Dickinson et al. |
| 10,292,722 B2 | 5/2019 | Brady et al. |
| 10,292,723 B2 | 5/2019 | Brady et al. |
| 10,299,811 B2 | 5/2019 | Brady et al. |
| 10,314,593 B2 | 6/2019 | Bardsley et al. |
| 10,327,781 B2 | 6/2019 | Divino et al. |
| 10,335,186 B2 | 7/2019 | Rosenbluth et al. |
| 10,342,571 B2 | 7/2019 | Marchand et al. |
| 10,349,960 B2 | 7/2019 | Quick |
| 10,357,265 B2 | 7/2019 | Brady et al. |
| 10,363,054 B2 | 7/2019 | Vale et al. |
| 10,390,850 B2 | 8/2019 | Vale et al. |
| 10,390,933 B2 | 8/2019 | Dickinson et al. |
| 10,398,580 B2 | 9/2019 | Dickinson et al. |
| 10,405,967 B1 | 9/2019 | Dickinson et al. |
| 10,420,570 B2 | 9/2019 | Vale et al. |
| 10,426,644 B2 | 10/2019 | Shrivastava et al. |
| 10,433,853 B2 | 10/2019 | Divino et al. |
| 10,433,992 B2 | 10/2019 | Wang et al. |
| 10,441,301 B2 | 10/2019 | Vale et al. |
| 10,456,151 B2 | 10/2019 | Slee et al. |
| 10,478,194 B2 | 11/2019 | Rhee et al. |
| 10,512,469 B2 | 12/2019 | Sutherland et al. |
| 10,517,617 B2 | 12/2019 | Aklog et al. |
| 10,517,622 B2 | 12/2019 | Vale et al. |
| 10,524,811 B2 | 1/2020 | Marchand et al. |
| 10,524,894 B1 | 1/2020 | Dickinson et al. |
| 10,543,308 B2 | 1/2020 | Lenihan et al. |
| 10,548,707 B2 | 2/2020 | Zaver et al. |
| 10,582,939 B2 | 3/2020 | Brady et al. |
| 10,588,648 B2 | 3/2020 | Brady et al. |
| 10,588,649 B2 | 3/2020 | Brady et al. |
| 10,588,655 B2 | 3/2020 | Rosenbluth et al. |
| 10,596,356 B2 | 3/2020 | Lenihan et al. |
| 10,610,246 B2 | 4/2020 | Brady et al. |
| 10,617,435 B2 | 4/2020 | Vale et al. |
| 10,653,426 B2 | 5/2020 | Yang et al. |
| 10,653,434 B1 | 5/2020 | Yang et al. |
| 10,667,833 B2 | 6/2020 | Vale et al. |
| 10,675,045 B2 | 6/2020 | Brady et al. |
| 10,682,152 B2 | 6/2020 | Vale et al. |
| 10,682,493 B2 | 6/2020 | Tran et al. |
| 10,695,159 B2 | 6/2020 | Hauser |
| 10,709,471 B2 | 7/2020 | Rosenbluth et al. |
| 10,722,257 B2 | 7/2020 | Skillrud et al. |
| 10,743,894 B2 | 8/2020 | Brady et al. |
| 10,743,895 B2 | 8/2020 | Losordo et al. |
| 10,772,649 B2 | 9/2020 | Hansen et al. |
| 10,786,270 B2 | 9/2020 | Yang et al. |

(56) References Cited

U.S. PATENT DOCUMENTS

| | | |
|---|---|---|
| 10,792,055 B2 | 10/2020 | Brady et al. |
| 10,792,056 B2 | 10/2020 | Vale et al. |
| 10,799,331 B2 | 10/2020 | Hauser |
| 10,806,611 B2 | 10/2020 | Cam et al. |
| 10,828,040 B2 | 11/2020 | Henkes et al. |
| 10,832,396 B2 | 11/2020 | Duffy et al. |
| 10,835,257 B2 | 11/2020 | Ferrera et al. |
| 10,835,271 B2 | 11/2020 | Ma |
| 10,835,367 B2 | 11/2020 | Dickinson et al. |
| 10,842,498 B2 | 11/2020 | Vale et al. |
| 10,912,577 B2 | 2/2021 | Marchand et al. |
| 10,932,802 B2 | 3/2021 | Goyal |
| 10,952,760 B2 | 3/2021 | Brady et al. |
| 11,000,682 B2 | 5/2021 | Merritt et al. |
| 11,045,204 B2 | 6/2021 | Cam et al. |
| 11,051,928 B2 | 7/2021 | Casey et al. |
| 11,058,445 B2 | 7/2021 | Cox et al. |
| 11,058,451 B2 | 7/2021 | Marchand et al. |
| 11,065,018 B2 | 7/2021 | Buck et al. |
| 11,076,876 B2 | 8/2021 | Vale |
| 11,077,129 B2 | 8/2021 | Sauve et al. |
| 11,077,135 B2 | 8/2021 | Baker et al. |
| 11,077,138 B2 | 8/2021 | Kang |
| 11,077,188 B2 | 8/2021 | Kauvar et al. |
| 11,077,285 B2 | 8/2021 | Martin |
| 11,083,475 B2 | 8/2021 | Kovarik et al. |
| 11,084,778 B2 | 8/2021 | Pelletier et al. |
| 11,085,083 B2 | 8/2021 | Barbeau et al. |
| 11,088,440 B2 | 8/2021 | Mccaughey et al. |
| 11,090,466 B1 | 8/2021 | Nicholson |
| 11,090,737 B2 | 8/2021 | Filho et al. |
| 11,096,712 B2 | 8/2021 | Teigen et al. |
| 11,103,264 B2 | 8/2021 | Vale et al. |
| 11,103,265 B2 | 8/2021 | Wallace et al. |
| 11,103,627 B2 | 8/2021 | Garrison et al. |
| 11,103,728 B2 | 8/2021 | Wang |
| 11,103,730 B2 | 8/2021 | Zwart et al. |
| 11,110,088 B2 | 9/2021 | Barf et al. |
| 11,110,524 B2 | 9/2021 | Fang et al. |
| 11,111,475 B2 | 9/2021 | Stice et al. |
| 11,114,269 B2 | 9/2021 | Bertsche et al. |
| 11,116,509 B2 | 9/2021 | Follmer et al. |
| 11,116,784 B2 | 9/2021 | Parikh |
| 11,116,943 B2 | 9/2021 | Deaton et al. |
| 11,123,089 B2 | 9/2021 | Ma |
| 11,123,090 B2 | 9/2021 | Yang et al. |
| 11,123,302 B2 | 9/2021 | Dayton et al. |
| 11,123,366 B1 | 9/2021 | Taraman et al. |
| 11,124,536 B2 | 9/2021 | Haydon et al. |
| 11,127,173 B2 | 9/2021 | Schafer et al. |
| 11,129,965 B2 | 9/2021 | Humbert et al. |
| 11,134,859 B2 | 10/2021 | Strasser et al. |
| 11,135,259 B2 | 10/2021 | Wu et al. |
| 11,141,071 B2 | 10/2021 | Moore et al. |
| 11,141,178 B2 | 10/2021 | Aboytes |
| 11,141,526 B2 | 10/2021 | Amato et al. |
| 11,143,352 B1 | 10/2021 | Tatarian |
| 11,145,110 B2 | 10/2021 | Story |
| 11,147,540 B2 | 10/2021 | Meyering et al. |
| 11,147,571 B2 | 10/2021 | Cox et al. |
| 11,147,572 B2 | 10/2021 | Vale et al. |
| 11,147,699 B2 | 10/2021 | Chou et al. |
| 11,147,890 B2 | 10/2021 | Polizzotti et al. |
| 11,147,949 B2 | 10/2021 | Yang et al. |
| 11,147,985 B2 | 10/2021 | Isola et al. |
| 11,148,213 B2 | 10/2021 | Bookheimer et al. |
| 11,149,922 B1 | 10/2021 | Reyes |
| 11,150,318 B2 | 10/2021 | Remelius |
| 11,150,561 B2 | 10/2021 | Cho et al. |
| 11,154,269 B2 | 10/2021 | Shea et al. |
| 11,154,314 B2 | 10/2021 | Quick |
| 11,154,356 B2 | 10/2021 | Gertner |
| 11,160,526 B2 | 11/2021 | Yu et al. |
| 11,160,572 B2 | 11/2021 | Ulm, III |
| 11,160,953 B2 | 11/2021 | Shimada et al. |
| 11,191,558 B2 | 12/2021 | Nguyen et al. |
| 11,197,683 B1 | 12/2021 | Teigen et al. |
| 11,241,304 B2 | 2/2022 | Dickinson et al. |
| 11,246,612 B2 | 2/2022 | Brady et al. |
| 11,253,278 B2 | 2/2022 | Casey et al. |
| 11,259,824 B2 | 3/2022 | Brady et al. |
| 11,266,427 B2 | 3/2022 | Duffy |
| 11,272,945 B2 | 3/2022 | Shrivastava et al. |
| 11,311,304 B2 | 4/2022 | Kelly et al. |
| 11,311,700 B2 | 4/2022 | Deaton et al. |
| 11,357,510 B2 | 6/2022 | Rhee et al. |
| 11,382,778 B2 | 7/2022 | Liebig et al. |
| 11,395,667 B2 | 7/2022 | Vale et al. |
| 11,406,403 B2 | 8/2022 | Casey et al. |
| 11,406,416 B2 | 8/2022 | Casey et al. |
| 11,433,218 B2 | 9/2022 | Quick et al. |
| 11,446,045 B2 | 9/2022 | Vale et al. |
| 11,446,170 B2 | 9/2022 | Dickinson et al. |
| 11,452,841 B2 | 9/2022 | Jalgaonkar et al. |
| 11,457,927 B2 | 10/2022 | Sutherland et al. |
| 11,464,528 B2 | 10/2022 | Brady et al. |
| 11,471,262 B2 | 10/2022 | Dickinson et al. |
| 11,478,614 B2 | 10/2022 | Deaton et al. |
| 11,484,328 B2 | 11/2022 | Gilvarry et al. |
| 11,523,838 B2 | 12/2022 | Nguyen et al. |
| 11,529,156 B2 | 12/2022 | Slee et al. |
| 11,529,157 B2 | 12/2022 | Brady et al. |
| 11,529,158 B2 | 12/2022 | Hauser |
| 11,547,427 B2 | 1/2023 | Vale et al. |
| 11,554,005 B2 | 1/2023 | Merritt et al. |
| 11,559,382 B2 | 1/2023 | Merritt et al. |
| 11,596,414 B2 | 3/2023 | Divino et al. |
| 11,612,397 B2 | 3/2023 | Hettel et al. |
| 11,642,145 B2 | 5/2023 | Vale et al. |
| 11,642,209 B2 | 5/2023 | Merritt et al. |
| 11,648,028 B2 | 5/2023 | Rosenbluth et al. |
| 11,660,426 B2 | 5/2023 | Nitzan et al. |
| 11,690,628 B2 | 7/2023 | Divino et al. |
| 11,690,741 B2 | 7/2023 | Cam et al. |
| 11,697,011 B2 | 7/2023 | Merritt et al. |
| 11,697,012 B2 | 7/2023 | Merritt et al. |
| 11,712,256 B2 | 8/2023 | Vale et al. |
| 11,744,691 B2 | 9/2023 | Merritt et al. |
| 11,779,364 B2 | 10/2023 | Casey et al. |
| 11,786,253 B2 | 10/2023 | Divino et al. |
| 11,786,254 B2 | 10/2023 | Ferrera et al. |
| 11,806,033 B2 | 11/2023 | Marchand et al. |
| 11,832,837 B2 | 12/2023 | Hauser |
| 11,832,838 B2 | 12/2023 | Hauser |
| 11,833,023 B2 | 12/2023 | Merritt et al. |
| 11,839,392 B2 | 12/2023 | Brady et al. |
| 11,839,393 B2 | 12/2023 | Hauser |
| 11,839,725 B2 | 12/2023 | Casey et al. |
| 11,844,921 B2 | 12/2023 | Merritt et al. |
| 11,849,963 B2 | 12/2023 | Quick |
| 11,850,379 B2 | 12/2023 | Humbert et al. |
| 11,857,209 B2 | 1/2024 | Choe et al. |
| 11,857,210 B2 | 1/2024 | Vale et al. |
| 11,864,770 B2 | 1/2024 | Bardsley et al. |
| 11,864,779 B2 | 1/2024 | Dinh |
| 11,864,781 B2 | 1/2024 | Shalgi et al. |
| 11,865,291 B2 | 1/2024 | Merritt et al. |
| 11,871,945 B2 | 1/2024 | Brady et al. |
| 11,871,947 B2 | 1/2024 | Losordo et al. |
| 11,871,949 B2 | 1/2024 | Brady et al. |
| 11,883,046 B2 | 1/2024 | Casey et al. |
| 11,890,180 B2 | 2/2024 | Merritt et al. |
| 11,918,243 B2 | 3/2024 | Marchand et al. |
| 11,918,244 B2 | 3/2024 | Marchand et al. |
| 11,925,369 B2 | 3/2024 | Hauser |
| 11,937,834 B2 | 3/2024 | Dinh |
| 11,937,835 B2 | 3/2024 | Vale et al. |
| 11,937,838 B2 | 3/2024 | Cox et al. |
| 11,944,327 B2 | 4/2024 | Vale et al. |
| 11,944,333 B2 | 4/2024 | Vale |
| 11,963,693 B2 | 4/2024 | Casey et al. |
| 11,963,861 B2 | 4/2024 | Strauss et al. |
| 11,969,178 B2 | 4/2024 | Hauser |
| 11,969,331 B2 | 4/2024 | Merritt et al. |

(56) References Cited

U.S. PATENT DOCUMENTS

| | | |
|---|---|---|
| 11,969,332 B2 | 4/2024 | Merritt et al. |
| 11,969,333 B2 | 4/2024 | Merritt et al. |
| 11,974,909 B2 | 5/2024 | Merritt et al. |
| 11,974,910 B2 | 5/2024 | Merritt et al. |
| 11,980,379 B2 | 5/2024 | Casey et al. |
| 11,980,537 B2 | 5/2024 | Merritt et al. |
| 11,986,382 B2 | 5/2024 | Merritt et al. |
| 11,998,223 B2 | 6/2024 | Brady et al. |
| 11,998,436 B2 | 6/2024 | Merritt et al. |
| 12,016,580 B2 | 6/2024 | Quick et al. |
| 12,016,582 B2 | 6/2024 | Nguyen et al. |
| 12,023,057 B2 | 7/2024 | Hauser |
| 12,029,441 B2 | 7/2024 | Bhogal et al. |
| 2004/0078334 A1 | 4/2004 | Malcolm et al. |
| 2005/0128096 A1 | 6/2005 | Adams |
| 2005/0227243 A1 | 10/2005 | Deak et al. |
| 2005/0277976 A1 | 12/2005 | Galdonik et al. |
| 2006/0187035 A1 | 8/2006 | Adams |
| 2007/0010787 A1 | 1/2007 | Hackett et al. |
| 2007/0269433 A1 | 11/2007 | Deak et al. |
| 2007/0287956 A1 | 12/2007 | Tal |
| 2008/0172717 A1 | 7/2008 | Malcolm |
| 2008/0301297 A1 | 12/2008 | Malcolm et al. |
| 2008/0301454 A1 | 12/2008 | Malcolm et al. |
| 2009/0024072 A1 | 1/2009 | Criado et al. |
| 2010/0042118 A1 | 2/2010 | Garrison et al. |
| 2013/0197567 A1 | 8/2013 | Brady et al. |
| 2013/0345739 A1 | 12/2013 | Brady et al. |
| 2014/0180397 A1 | 6/2014 | Gerberding et al. |
| 2014/0200608 A1 | 7/2014 | Brady et al. |
| 2014/0277079 A1 | 9/2014 | Vale et al. |
| 2014/0288588 A1 | 9/2014 | Cang et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0147520 A1 | 5/2015 | Grau |
| 2015/0164523 A1 | 6/2015 | Brady et al. |
| 2015/0173782 A1 | 6/2015 | Garrison et al. |
| 2015/0257775 A1 | 9/2015 | Gilvarry et al. |
| 2015/0359547 A1 | 12/2015 | Vale et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0151550 A1 | 6/2016 | Fisher et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vald et al. |
| 2016/0317168 A1 | 11/2016 | Brady et al. |
| 2016/0378943 A1 | 12/2016 | Vallee |
| 2017/0043066 A1 | 2/2017 | Laub |
| 2017/0071614 A1 | 3/2017 | Vale et al. |
| 2017/0086862 A1 | 3/2017 | Vale et al. |
| 2017/0086863 A1 | 3/2017 | Brady et al. |
| 2017/0105743 A1* | 4/2017 | Vale ................ A61B 17/22032 |
| 2017/0112515 A1 | 4/2017 | Brady et al. |
| 2017/0215903 A1 | 8/2017 | Vale et al. |
| 2017/0265878 A1 | 9/2017 | Marchand et al. |
| 2018/0052965 A1 | 2/2018 | Tumkur et al. |
| 2018/0092652 A1 | 4/2018 | Marchand et al. |
| 2018/0132876 A1 | 5/2018 | Zaidat |
| 2018/0193026 A1 | 7/2018 | Yang et al. |
| 2018/0193043 A1 | 7/2018 | Marchand et al. |
| 2018/0263632 A1 | 9/2018 | Seifert et al. |
| 2018/0280623 A1 | 10/2018 | Pilkington et al. |
| 2018/0296240 A1 | 10/2018 | Rosenbluth et al. |
| 2018/0344338 A1 | 12/2018 | Brady et al. |
| 2018/0344339 A1 | 12/2018 | Cox et al. |
| 2018/0360483 A1 | 12/2018 | Brady et al. |
| 2018/0361116 A1 | 12/2018 | Quick et al. |
| 2019/0000492 A1 | 1/2019 | Casey et al. |
| 2019/0046219 A1 | 2/2019 | Marchand et al. |
| 2019/0070401 A1 | 3/2019 | Merritt et al. |
| 2019/0142442 A1 | 5/2019 | Vale et al. |
| 2019/0150959 A1 | 5/2019 | Cox et al. |
| 2019/0167287 A1 | 6/2019 | Vale |
| 2019/0201014 A1 | 7/2019 | Vale |
| 2019/0223893 A1 | 7/2019 | Gilvarry et al. |
| 2019/0231372 A1 | 8/2019 | Brady et al. |
| 2019/0231373 A1 | 8/2019 | Quick |
| 2019/0239907 A1 | 8/2019 | Brady et al. |
| 2019/0239908 A1 | 8/2019 | Brady et al. |
| 2019/0239910 A1 | 8/2019 | Brady et al. |
| 2019/0239911 A1 | 8/2019 | Zaidat |
| 2019/0298397 A1 | 10/2019 | Vale et al. |
| 2019/0321071 A1 | 10/2019 | Marchand et al. |
| 2019/0328411 A1 | 10/2019 | Vale et al. |
| 2019/0336151 A1 | 11/2019 | Vale et al. |
| 2019/0365399 A1 | 12/2019 | Vale et al. |
| 2019/0374238 A1 | 12/2019 | Vale et al. |
| 2019/0381223 A1 | 12/2019 | Culbert et al. |
| 2020/0000483 A1 | 1/2020 | Brady et al. |
| 2020/0001046 A1 | 1/2020 | Yang et al. |
| 2020/0008820 A1 | 1/2020 | Aboytes et al. |
| 2020/0009301 A1 | 1/2020 | Yee |
| 2020/0046368 A1 | 2/2020 | Merritt et al. |
| 2020/0046390 A1 | 2/2020 | Brady et al. |
| 2020/0060703 A1 | 2/2020 | Vale et al. |
| 2020/0069889 A1 | 3/2020 | Lin |
| 2020/0085444 A1 | 3/2020 | Vale et al. |
| 2020/0100804 A1 | 4/2020 | Casey et al. |
| 2020/0107851 A1 | 4/2020 | Mccarthy |
| 2020/0121339 A1 | 4/2020 | Brady et al. |
| 2020/0126212 A1 | 4/2020 | Duffy et al. |
| 2020/0138460 A1 | 5/2020 | Yang et al. |
| 2020/0155181 A1 | 5/2020 | Yang et al. |
| 2020/0155293 A1 | 5/2020 | Morrison et al. |
| 2020/0205845 A1 | 7/2020 | Yang et al. |
| 2020/0246031 A1 | 8/2020 | Vale et al. |
| 2020/0281611 A1 | 9/2020 | Kelly et al. |
| 2020/0281612 A1 | 9/2020 | Kelly et al. |
| 2020/0289136 A1 | 9/2020 | Chou |
| 2020/0297972 A1 | 9/2020 | Yee et al. |
| 2020/0305900 A1 | 10/2020 | Vale et al. |
| 2020/0306501 A1 | 10/2020 | Yee et al. |
| 2020/0323615 A1 | 10/2020 | Casey et al. |
| 2020/0345904 A1 | 11/2020 | Casey et al. |
| 2020/0353205 A1 | 11/2020 | Kelly et al. |
| 2020/0353226 A1 | 11/2020 | Keating et al. |
| 2020/0353228 A1 | 11/2020 | Casey et al. |
| 2020/0353229 A1 | 11/2020 | Casey et al. |
| 2020/0390459 A1 | 12/2020 | Casey et al. |
| 2020/0390460 A9 | 12/2020 | Casey et al. |
| 2020/0390515 A1 | 12/2020 | Lorenzo |
| 2021/0007757 A1 | 1/2021 | Casey et al. |
| 2021/0038227 A1 | 2/2021 | Vale et al. |
| 2021/0069468 A1 | 3/2021 | Keating et al. |
| 2021/0077134 A1 | 3/2021 | Vale et al. |
| 2021/0106238 A1 | 4/2021 | Strasser et al. |
| 2021/0113224 A1 | 4/2021 | Dinh |
| 2021/0121165 A1 | 4/2021 | Duffy et al. |
| 2021/0128183 A1 | 5/2021 | Lee |
| 2021/0145447 A1 | 5/2021 | Stefanov |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0154443 A1 | 5/2021 | Casey |
| 2021/0161544 A1 | 6/2021 | Casey |
| 2021/0186536 A1 | 6/2021 | Buck et al. |
| 2021/0186537 A1 | 6/2021 | Buck et al. |
| 2021/0186541 A1 | 6/2021 | Thress |
| 2021/0186542 A1 | 6/2021 | Buck et al. |
| 2021/0187244 A1 | 6/2021 | Buck et al. |

(56) References Cited

U.S. PATENT DOCUMENTS

| | | |
|---|---|---|
| 2021/0187264 A1 | 6/2021 | Lee et al. |
| 2021/0196292 A1 | 7/2021 | Vale |
| 2021/0228223 A1 | 7/2021 | Casey et al. |
| 2021/0236148 A1 | 8/2021 | Marchand et al. |
| 2021/0259720 A1 | 8/2021 | Brady et al. |
| 2021/0267745 A1 | 9/2021 | Walzman |
| 2021/0268311 A1 | 9/2021 | Park et al. |
| 2021/0268591 A1 | 9/2021 | Filho et al. |
| 2021/0270847 A1 | 9/2021 | Wang et al. |
| 2021/0274635 A1 | 9/2021 | Cooley et al. |
| 2021/0275197 A1 | 9/2021 | Vale et al. |
| 2021/0275198 A1 | 9/2021 | Keating et al. |
| 2021/0275783 A1 | 9/2021 | Johnson et al. |
| 2021/0275833 A1 | 9/2021 | Krishnaswamy et al. |
| 2021/0277052 A1 | 9/2021 | Gewirth et al. |
| 2021/0277453 A1 | 9/2021 | Shapiro et al. |
| 2021/0282735 A1 | 9/2021 | Wiggers et al. |
| 2021/0282944 A1 | 9/2021 | Chen et al. |
| 2021/0283080 A1 | 9/2021 | Gwag et al. |
| 2021/0283426 A1 | 9/2021 | Carabe-Fernandez et al. |
| 2021/0286845 A1 | 9/2021 | Dowler et al. |
| 2021/0290194 A1 | 9/2021 | Bai et al. |
| 2021/0290822 A1 | 9/2021 | Seal et al. |
| 2021/0290907 A1 | 9/2021 | Martin |
| 2021/0290925 A1 | 9/2021 | Merritt et al. |
| 2021/0290979 A1 | 9/2021 | Liu et al. |
| 2021/0291280 A1 | 9/2021 | Silva et al. |
| 2021/0292293 A1 | 9/2021 | Kusama et al. |
| 2021/0295339 A1 | 9/2021 | Adjaoute |
| 2021/0295590 A1 | 9/2021 | Decell et al. |
| 2021/0296303 A1 | 9/2021 | Cho et al. |
| 2021/0298601 A1 | 9/2021 | Federoff et al. |
| 2021/0298889 A1 | 9/2021 | Casey et al. |
| 2021/0299214 A1 | 9/2021 | Jay et al. |
| 2021/0299435 A1 | 9/2021 | Simon et al. |
| 2021/0304402 A1 | 9/2021 | Morgas et al. |
| 2021/0307766 A1 | 10/2021 | Keating et al. |
| 2021/0308209 A1 | 10/2021 | Tymianski |
| 2021/0308358 A1 | 10/2021 | Raman et al. |
| 2021/0308486 A1 | 10/2021 | Perez et al. |
| 2021/0309730 A1 | 10/2021 | Schaefer et al. |
| 2021/0315594 A1 | 10/2021 | Kallmes et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0315599 A1 | 10/2021 | Vale et al. |
| 2021/0316116 A1 | 10/2021 | Kallmes et al. |
| 2021/0316121 A1 | 10/2021 | Buck et al. |
| 2021/0316127 A1 | 10/2021 | Buck et al. |
| 2021/0316158 A1 | 10/2021 | Shaw et al. |
| 2021/0316376 A1 | 10/2021 | Filho et al. |
| 2021/0316500 A1 | 10/2021 | Skelton et al. |
| 2021/0321961 A1 | 10/2021 | Harrison et al. |
| 2021/0322036 A1 | 10/2021 | Anushree et al. |
| 2021/0322037 A1 | 10/2021 | Anushree et al. |
| 2021/0322038 A1 | 10/2021 | Dwivedi et al. |
| 2021/0322773 A1 | 10/2021 | Beufer et al. |
| 2021/0322787 A1 | 10/2021 | Stahl et al. |
| 2021/0323082 A1 | 10/2021 | Bookheimer et al. |
| 2021/0323955 A1 | 10/2021 | Panicker et al. |
| 2021/0326932 A1 | 10/2021 | Chu |
| 2021/0330332 A1 | 10/2021 | Chou et al. |
| 2021/0330344 A1 | 10/2021 | Rosenbluth et al. |
| 2021/0330371 A1 | 10/2021 | Gunther et al. |
| 2021/0334960 A1 | 10/2021 | Arnold et al. |
| 2021/0338256 A1 | 11/2021 | Chou et al. |
| 2021/0338854 A1 | 11/2021 | Nissenbaum et al. |
| 2021/0340341 A1 | 11/2021 | Jackson et al. |
| 2021/0341180 A1 | 11/2021 | Kirscht |
| 2021/0378694 A1 | 12/2021 | Thress et al. |
| 2022/0039815 A1 | 2/2022 | Thress et al. |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0346813 A1 | 11/2022 | Quick |
| 2023/0218310 A1 | 7/2023 | Scheinblum et al. |
| 2023/0218313 A1 | 7/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0310137 A1 | 10/2023 | Merritt et al. |
| 2023/0310751 A1 | 10/2023 | Merritt et al. |
| 2023/0329734 A1 | 10/2023 | Marchand et al. |
| 2023/0355256 A1 | 11/2023 | Dinh |
| 2023/0355938 A1 | 11/2023 | Merritt et al. |
| 2023/0363776 A1 | 11/2023 | Quick |
| 2023/0389932 A1 | 12/2023 | Ozenne et al. |
| 2024/0074771 A1 | 3/2024 | Quick et al. |
| 2024/0082540 A1 | 3/2024 | Brodt et al. |
| 2024/0157041 A1 | 5/2024 | Zikry et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |

FOREIGN PATENT DOCUMENTS

| | | |
|---|---|---|
| CN | 108601599 B | 8/2021 |
| CN | 111012443 B | 9/2022 |
| EP | 3593742 A1 | 1/2020 |
| EP | 3335647 B1 | 1/2022 |
| ES | 2932031 T3 | 1/2023 |
| JP | 7389159 B2 | 11/2023 |
| WO | 2018/019829 A1 | 2/2018 |

OTHER PUBLICATIONS

De Marini et al., "A Direct Aspiration First Pass Technique with The New ARC Catheter for Thrombectomy of Large Vessel Occlusion Strokes: A Multicenter Study", vol. 25, Issue 2, World Federation of Interventional and Therapeutic Neuroradiology, Oct. 5, 2018, Online Available at: https://doi.org/10.1177/1591019918803962, pp. 187-193.

Donaldson et al., "Thrombectomy Using Suction Filtration and Veno-Venous Bypass: Single Center Experience With A Novel Device", vol. 86, Issue 2, online available at: https://doi.org/10.1002/ccd.25583, pp. E81-E87.

Froehler, Michael T., "Comparison of Vacuum Pressures and Forces Generated by Different Catheters and Pumps for Aspiration Thrombectomy in Acute Ischemic Stroke", Interventional Neurology, vol. 6, Issue 3-4, Oct. 2017, Online Available at: https://doi.org/10.1159/000475478, pp. 199-206.

Heberlein et al., "New Generation Aspiration Catheter: Feasibility in The Treatment of Pulmonary Embolism", World Journal of Radiology, vol. 5, Issue 11, Nov. 18, 2013, pp. 430-435.

Möhlenbruch et al., "Multicenter Experience with The New SOFIA Plus Catheter As A Primary Local Aspiration Catheter For Acute Stroke Thrombectomy", Journal of Neurointerventional Surgery, vol. 9, Issue 12, Dec. 2017, Online Available at: https://doi.org/10.1136/neurintsurg-2016-012812, pp. 1223-1227.

Nikoubashman et al., "Necessary Catheter Diameters for Mechanical Thrombectomy with ADAPT", American Journal of Neuroradiology, vol. 38 Issue 12, Aug. 29, 2024, pp. 2277-2281.

Nikoubashman et al., "Under Pressure: Comparison of Aspiration Techniques for Endovascular Mechanical Thrombectomy", American Journal of Neuroradiology, vol. 39, May 2018, pp. 905-909.

Turk et al., "ADAPT FAST Study: A Direct Aspiration first Pass Technique for Acute Stroke Thrombectomy", Journal of Neurointerventional Surgery, vol. 6, 2014, pp. 260-264.

Zehnder et al., "Percutaneous Catheter Thrombus Aspiration for Acute or Subacute Arterial Occlusion of the Legs: How Much Thrombolysis is Needed?", European Journal of Vascular and Endovascular Surgery, vol. 20, 2000, pp. 41-46.

WIPO, "International Search Report and Written Opinion" issued in connection with PCT Patent Application PCT/US2023/064167, dated Oct. 20, 2023, 13 pages.

Shani et al., "Mechanical Manipulation of Thrombus: Coronary Thrombectomy," Intracoronary Clot Displacement, and Transcatheter Aspiration, American Journal of Cardiology, vol. 72, Dec. 16, 1993, pp. 116G-118G.

(56) References Cited

OTHER PUBLICATIONS

Bose et al., "The Penumbra System: A Mechanical Device for the Treatment of Acute Stroke due to Thromboembolism", American Journal of Neuroradiology. vol. 29, Aug. 2008, pp. 1409-1413.

Turk et al., "Initial Clinical Experience with The ADAPT Technique: A Direct Aspiration First Pass Technique for Stroke Thrombectomy," Journal of NeuroInterventional Surgery, 2013, 9 pages.

Turk III et al., "Aspiration Thrombectomy Versus Stent Retriever Thrombectomy As First-Line Approach For Large Vessel Occlusion (COMPASS): A Multicentre, Randomized, Open Label, Blinded Outcome, Non-Inferiority Trial", Lancet, vol. 393, Mar. 9, 2019, pp. 998-1008.

Saver, Jeffrey L., "Time is Brain—Quantified," Stroke, Center and Department of Neurology, vol. 37, 2006, pp. 263-266.

Horowitz et al., "In Vitro Proof of Concept Evaluation of a Gravity Powered Novel Filtration Device to Effectively Process a Blood Analogue/Particle Mixture to Rapidly Produce a Clear Filtrate", Cardiology and Cardiovascular Medicine, Fortune Journals, vol. 8, Issue 1, 2004, pp. 48-51.

Horowitz et al., "Extra-Corporeal Processing of Bovine, Porcine and Human Blood in Preparation for Autologous Re-Infusion Using a Disposable Filtration System: Initial Proof of Concept Study and Potential Applications for Human Autologous Blood Reinfusion in the Civilian and Combat Casualty Care Settings", Journal of Biology and Today's World 2023, vol. 12, Issue 06, 2023, pp. 1-6.

Ipcard Cardiac Care, "Export Advance—A Thrombus Aspiration Cather", Online Available at: https://www.youtube.com/watch?v=ymp8uNtFfM0, Retrieved on Nov. 21, 2024, 2 pages.

Merit Medical, "ASAP Aspiration Cather", Instructions for Use, in English, French, Spanish and Portuguese Languages, Received on Nov. 19, 2024, 7 pages.

Merit Medical, "ASAP Aspiration Cather", Online Available at: https://www.youtube.com/watch?v=rYxNUN_uRXE, Retrieved on Nov. 21, 2024, 3 pages.

\* cited by examiner

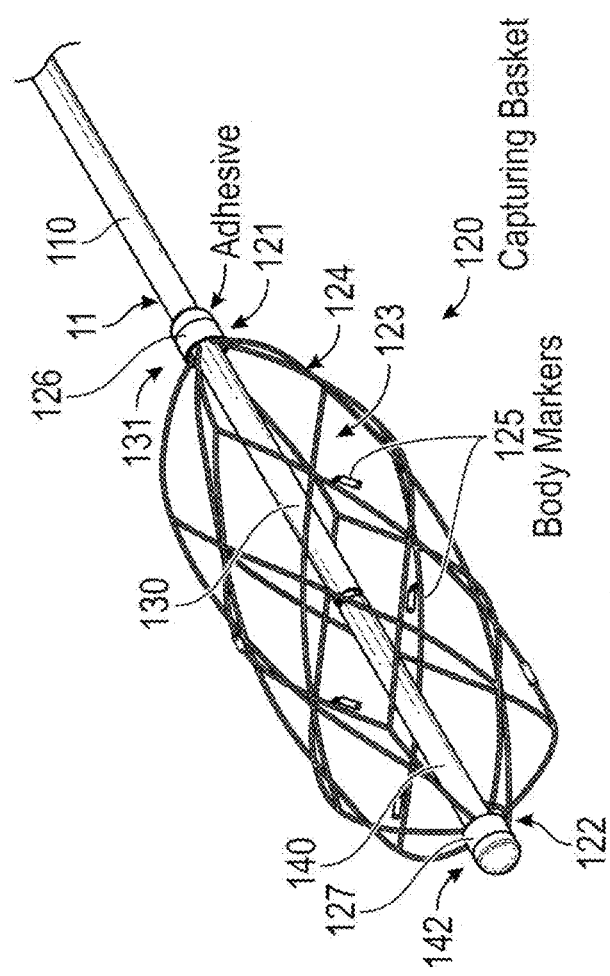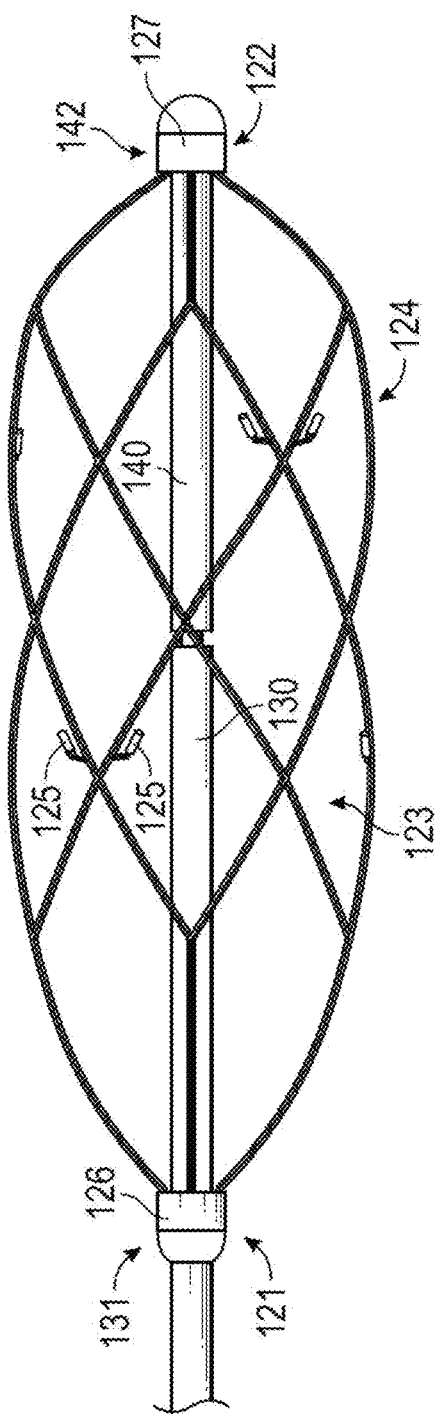

DEVICES AND METHODS FOR REMOVING AN EMBOLUS

CROSS-REFERENCES TO RELATED APPLICATIONS

This application is a continuation-in-part and claims benefit of U.S. patent application Ser. No. 16/597,727 filed Oct. 9, 2019, now U.S. Pat. No. 11,272,945, which is a non-provisional application and claims benefit of U.S. Provisional Application No. 62/744,107 filed Oct. 10, 2018, the specification(s) of which is/are incorporated herein in their entirety by reference.

FIELD OF THE INVENTION

The present invention relates to the field of medical devices and methods that remove emboli.

BACKGROUND OF THE INVENTION

In recent years, clot retrieval has been proven to be a safe and effective treatment for acute ischemic stroke patients. In spite of the success of clot retrieval as a treatment for acute ischemic stroke, treatments for diseases that are created by the presence of large clots such as pulmonary embolism (PE) have seen very limited progress. More than 300,000 patients are hospitalized for PE each year in the United States alone and 100,000 deaths result from PE each year.

Pulmonary embolism often occurs when a clot that is formed in deep veins, travels to the lungs and blocks pulmonary arteries. The presence of a pulmonary embolus can cut off blood to large portions of the lungs and be potentially fatal. Clot burden is often high causing a blockage in the main pulmonary artery and/or left and/or right pulmonary arteries and their branches. Emboli are particularly difficult to remove because they are often large in size and need to traverse a complex and tortuous pathway to be extracted out of the body using an endovascular approach. Pulmonary embolism can cause right heart strain resulting in heart failure leading to death in many cases.

PE is different from acute ischemic stroke in that clot burden is often much higher in PE. This creates a need for medical devices that can retrieve large clots out of the body safely and quickly thereby opening the passage for deoxygenated blood to travel to the lungs. Therefore, there is a need for a method and device that safely removes embolic mass from pulmonary arteries.

BRIEF SUMMARY OF THE INVENTION

It is an objective of the present invention to provide systems, devices, and methods that allow for retrieving a clot in a vessel, as specified in the independent claims. Embodiments of the invention are given in the dependent claims. Embodiments of the present invention can be freely combined with each other if they are not mutually exclusive.

In some embodiments, the present invention features a capturing basket for capturing an embolus. The capturing basket comprises a first basket end and a second basket end, a plurality of cells defined by struts, and at least four body markers disposed on the basket. In some embodiments, the struts have strut ends that are connected to the first basket end and the second basket end.

In other embodiments, the present invention may also feature a clot retrieval device. The clot retrieval device may comprise a delivery shaft (e.g., a pusher), a capturing basket, and a support component. The delivery shaft (e.g., a pusher) has a distal delivery shaft end. In some embodiments, the capturing basket is coupled to the distal delivery shaft end. The capturing basket comprises a first basket end, a second basket end, a plurality of cells defined by struts, and at least four body markers disposed on the basket. The struts may have strut ends that are connected to the first basket end and the second basket end. In some embodiments, the support component is coupled to the distal delivery shaft end and disposed within the capturing basket.

One of the unique and inventive technical features of the present invention is the shape and dimensions of the plurality of closed cells that make up the capturing basket. Without wishing to limit the invention to any theory or mechanism, it is believed that the technical feature of the present invention advantageously provides for an embolus to ingress into the capturing basket. Additionally, the clot retrieval devices described herein are configured to withstand torque (i.e., are configured to rotate). Specifically, when the distal end of a delivery shaft (e.g., a pusher) described herein is hand-rotated (e.g., axially rotated) is torque transferred through the delivery shaft (110) to the capturing basket (120), such that the capturing basket (120) is also rotated. Without wishing to limit the invention to any theory or mechanism, it is believed that the technical feature of the present invention advantageously enables controlled shearing of the embolus by the capturing basket and allows for the capturing basket to dislodge an embolus from a vessel wall. None of the presently known prior references or work has the unique, inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A and 1B show clot retrieval devices as described herein. FIG. 1A shows a schematic drawing of the clot retrieval device described herein, either comprising a delivery sheath (top) or a delivery catheter (bottom). FIG. 1B shows a clot retrieval device.

FIG. 2 shows a detailed clot retrieval device in accordance with embodiments herein.

FIGS. 3A, 3B, and 3C show various embodiments of the capturing basket described herein. FIG. 3A shows a capturing basket in which the body markers are aligned with the struts of the capturing basket. FIGS. 3B and 3C show capturing baskets in which the body markers are protruded from the struts of the capturing basket.

FIGS. 6A, 6B, 6C, and 6D show rudimentary diagrams of how parts of a support component described herein (e.g., a support component comprising a first support portion, a second support portion, and an inner shaft disposed through the first lumen of the first support portion and the second lumen of the second support portion) may move in accordance with embodiments herein.

Figure 7:
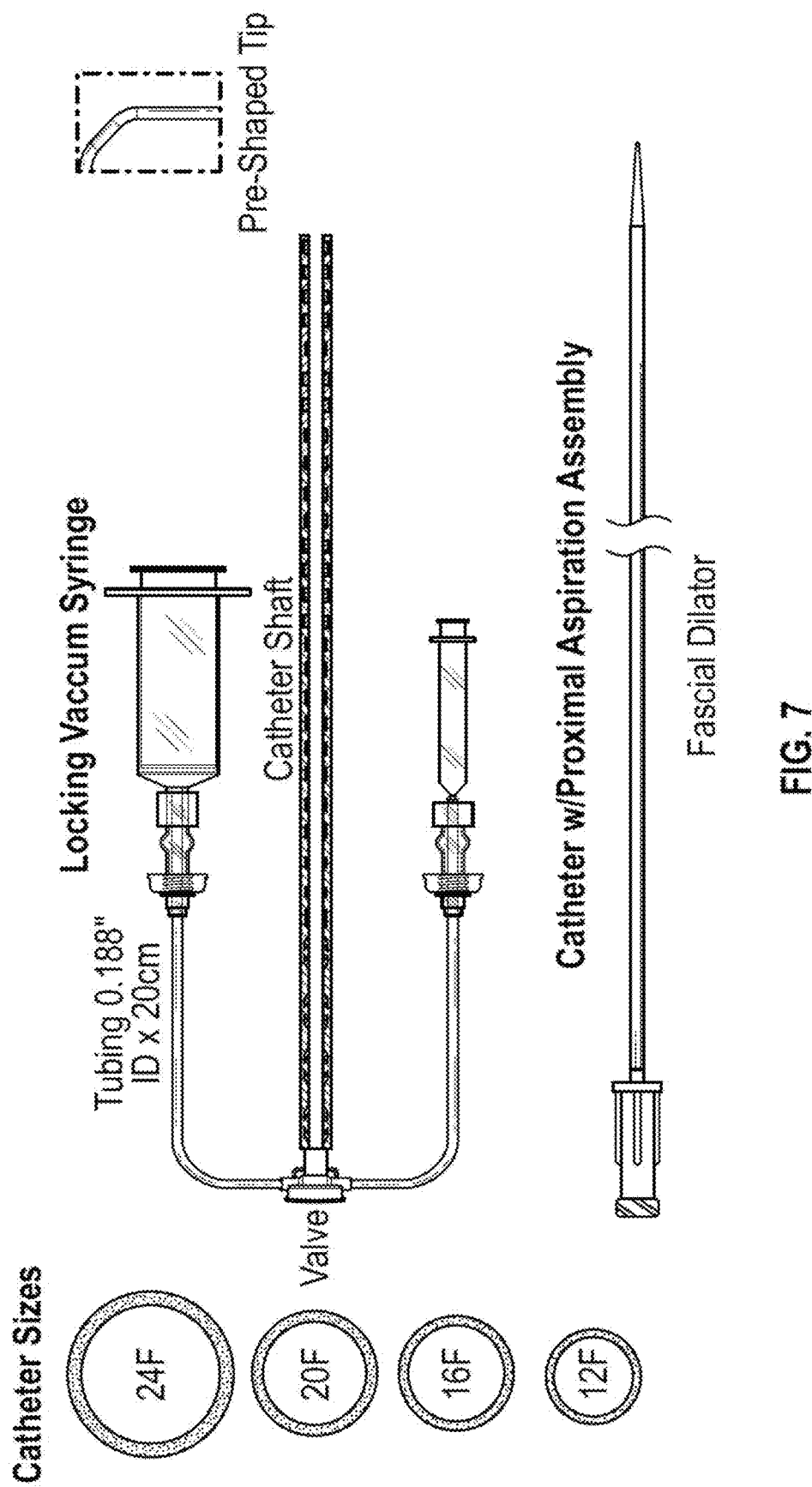

FIG. 7 shows, in accordance with embodiments herein, a delivery catheter. The catheter shaft may comprise an attached hub sub-assembly. In addition, a dilator may be used in conjunction with the catheter described herein.

Figure 8:
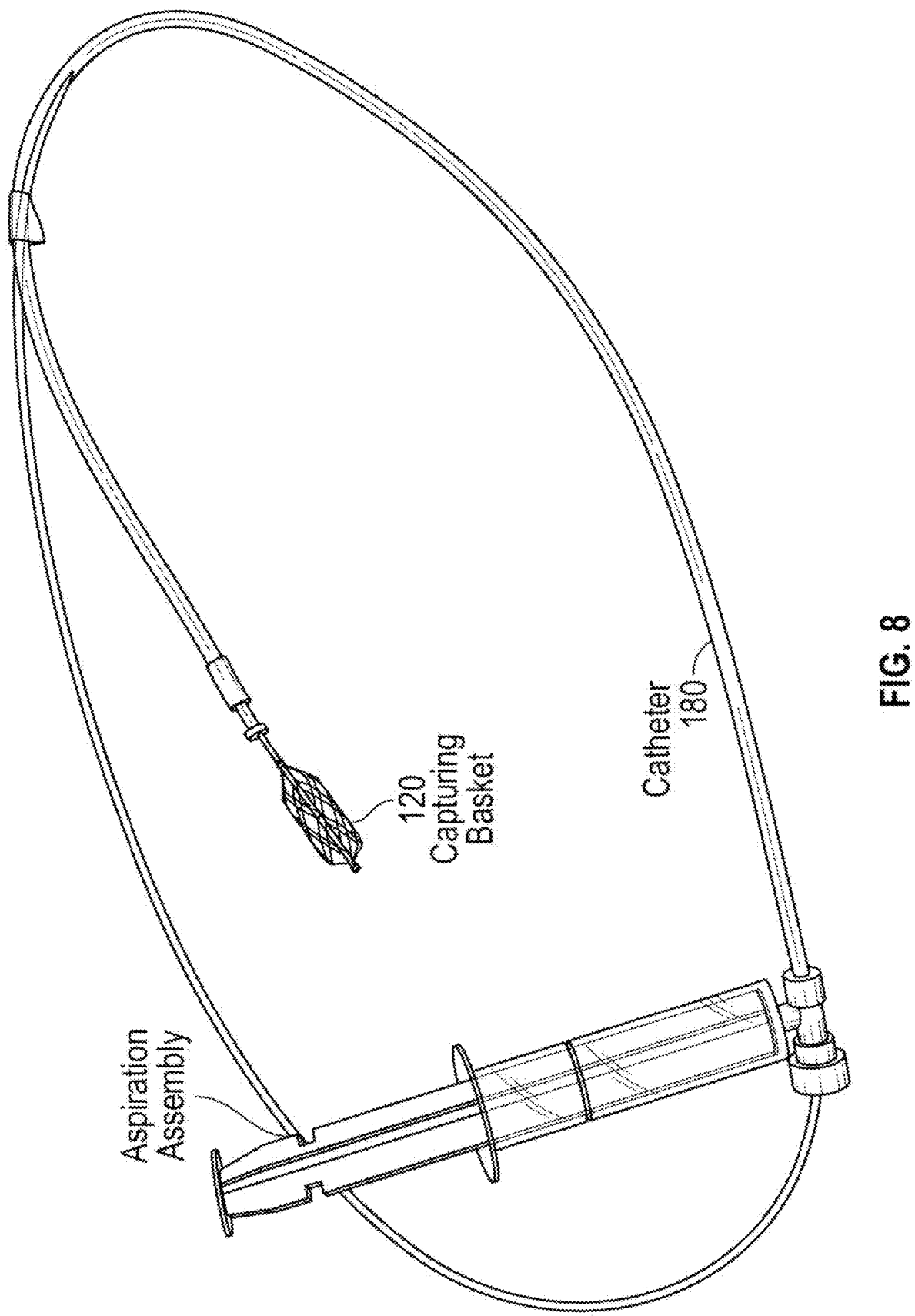

FIG. 8 shows the clot retrieval device assembly, including a delivery catheter.

Figure 9A:
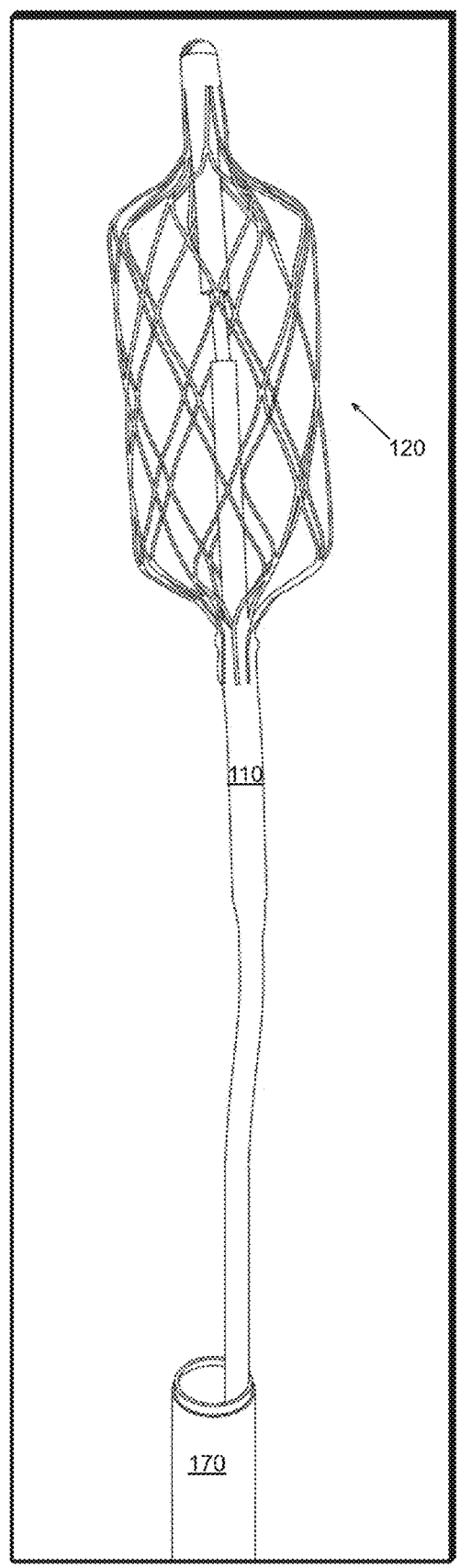
Figure 9B:
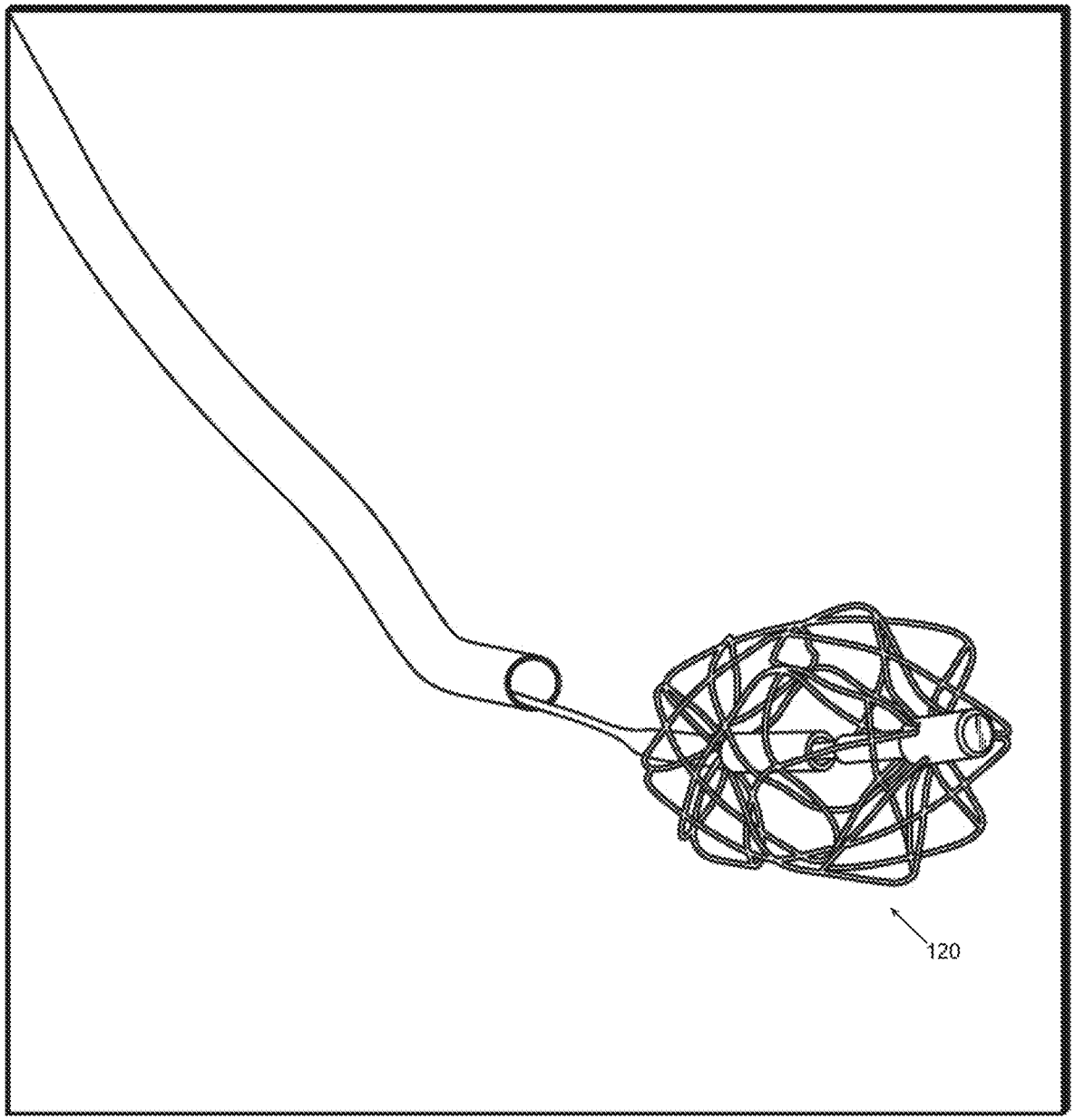

FIGS. 9A and 9B show alternate views of the clot retrieval device, specifically the capturing basket.

Figure 10:
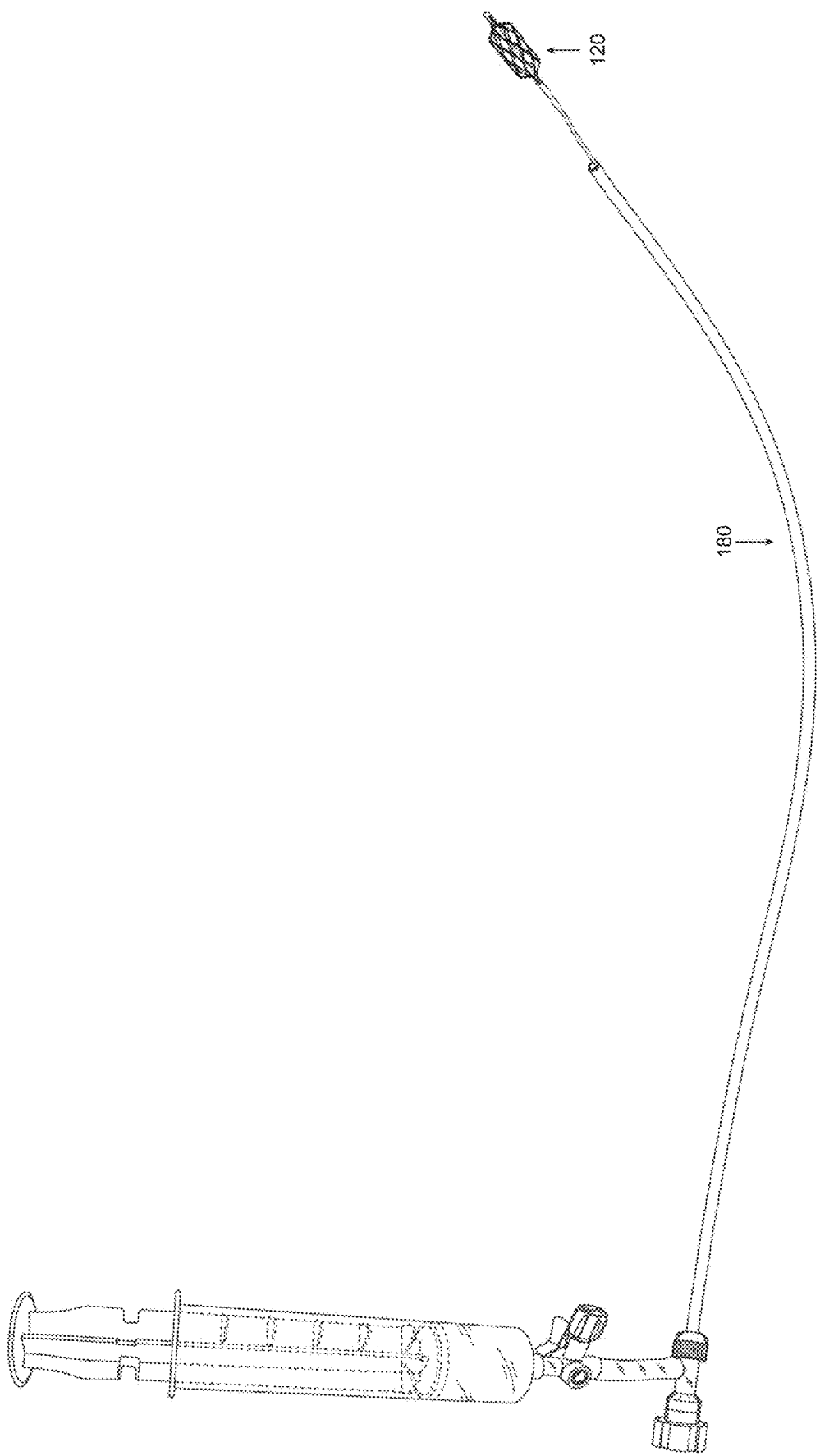

FIG. 10 shows the clot retrieval device comprising a catheter

DETAILED DESCRIPTION OF THE INVENTION

Following is a list of elements corresponding to a particular element referred to herein:
- 100 Clot Retrieval Device
- 110 Delivery Shaft
- 111 Distal Delivery Shaft End
- 120 Capturing Basket
- 121 First Basket End
- 122 Second Basket End
- 123 Cells
- 124 Struts
- 125 Body Markers
- 126 First Marker
- 127 Second Marker
- 150 Support Component
- 130 First Support Portion
- 131 First End
- 132 Second End
- 133 First Lumen
- 140 Second Support Portion
- 141 First End
- 142 Second End
- 143 Second Lumen
- 160 Inner Shaft
- 170 Delivery Sheath
- 180 Delivery Catheter Referring now to FIGS. 1A-10, the present invention features devices and methods for trapping and retrieving an embolus.

In some embodiments, the present invention features a capturing basket (120) for capturing an embolus. The capturing basket comprises a first basket end (121) and a second basket end (122). In some embodiments, the capturing basket (120) comprises a plurality of cells (123) defined by struts (124) and at least four body markers (125) disposed on the basket. The struts may have strut ends that are connected to the first basket end (121) and the second basket end (122).

In some embodiments, the present invention may also feature a clot retrieval device (100). The clot retrieval device (100) may comprise a delivery shaft (110; e.g., a pusher), a capturing basket (120), and a support component (150). The delivery shaft (110; e.g., a pusher) has a distal delivery shaft end (111). In some embodiments, the capturing basket (120) is coupled to the distal delivery shaft end (111). The capturing basket (120) comprises a first basket end (121), a second basket end (122), a plurality of cells (123) defined by struts (124), and at least four body markers (125) disposed on the basket. The struts may have strut ends that are connected to the first basket end (121) and the second basket end (122). In some embodiments, the support component (150) is coupled to the distal delivery shaft end (111) and disposed within the capturing basket (120).

In some embodiments, the support component (150) comprises a first support portion (130) comprising a first end (131), a second end (132), and a first lumen (133). In some embodiments, the first end (131) of the first support portion (130) is disposed within the basket (120) proximal to the first basket end (121).

In other embodiments, the support component (150) comprises a second support portion (140) comprising a first end (141), a second end (142), and a second lumen (143). In some embodiments, the second end (142) of the second support portion (140) is disposed within the basket (120) proximal to the second basket end (122). In some embodiments, the second end (132) of the first support portion (130) is adjacent to the first end (141) of the second support portion (140). In some embodiments, the second end (142) of the second support portion (140) is fixed to the second basket end (122) of the capturing basket (120).

In some embodiments, the support component (150) further comprises an inner shaft (160) disposed through the first lumen (133) of the first support portion (130) and the second lumen (143) of the second support portion (140).

In some embodiments, the inner shaft (160) is movable. In some embodiments, the inner shaft (160) is free-floating and is not affixed to either end (i.e., not affixed to the first end (131) of the first support portion (130) or to the second end (142) of the second support portion (140)). In some embodiments, the inner shaft (160) is free-floating inside the first lumen (133) of the first support portion (130) and the second lumen (143) of the second support portion (140). In other embodiments, the inner shaft (160) is affixed to the second end (142; e.g., the distal end) of the second support portion (140). In further embodiments, the inner shaft (160) is affixed to the first end (131; e.g., the proximal end) of the first support portion (130). In certain embodiments, the inner shaft (160) is affixed to the first end (131; e.g., the proximal end) of the first support portion (130) and affixed to the second end (142; e.g., the distal end) of the second support portion (140).

Figure 6A:
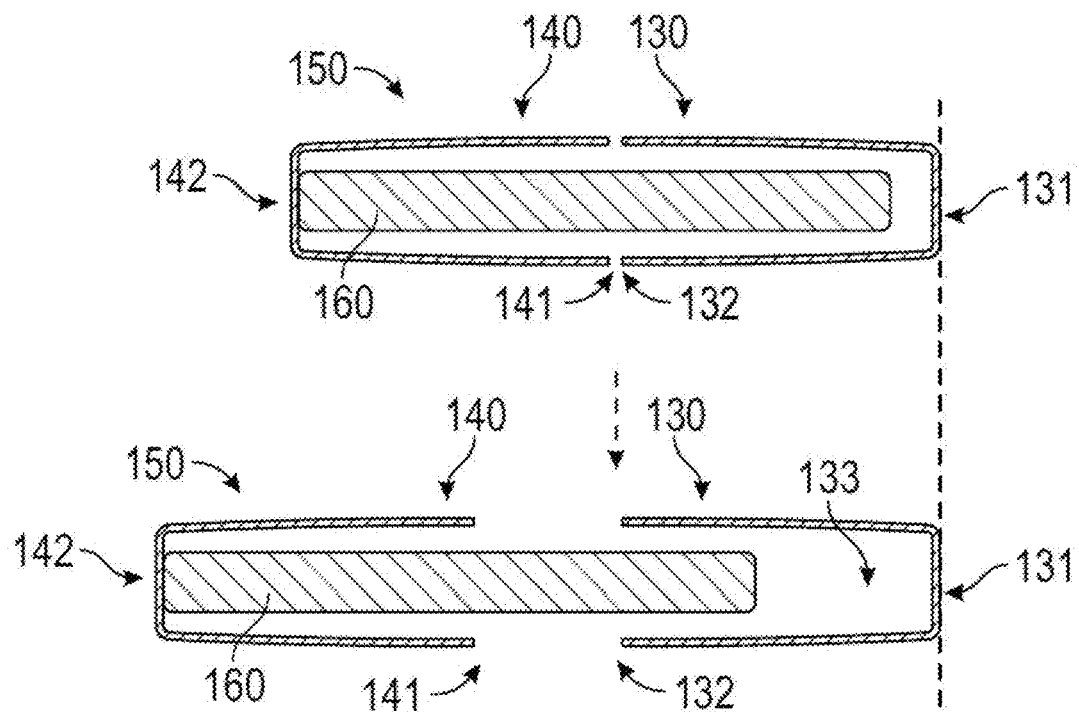

In some embodiments, the clot retrieval devices (100) described herein comprise an inner shaft (160) affixed to the second end (142; e.g., the distal end) of the second support portion (140) (see FIG. 6A). This allows the second support portion (140) to be movable relative to the first support portion (130) and allows for the inner shaft (160) to slide within the first lumen (133) of the first support portion (130). In some embodiments, the first support portion (130) is stationary relative to the delivery shaft (110). In some embodiments, the first end (131) of the first support portion (130) is fixed to the distal delivery shaft end (111) of the delivery shaft (110). When the inner shaft (160) slides distally within the first lumen (133) of the first support portion (130), away from the first end (131) of the support portion (130), the capturing basket (120) elongates (i.e., the second basket end (122) moves away (i.e., distally) from the first basket end (121)). The inner shaft sliding distally within the first lumen (133) of the first support portion (130) causes the second end (142) of the second support portion (140) to also extend distally, away from the first support portion (130). Additionally, when the inner shaft (160) slides proximally within the first lumen (133) of the first support portion (130), towards the first end (131) of the support portion (130), the capturing basket (120) collapses (i.e., the second basket end (122) moves towards (i.e., proximally) the first basket end (121)).

Figure 6B:
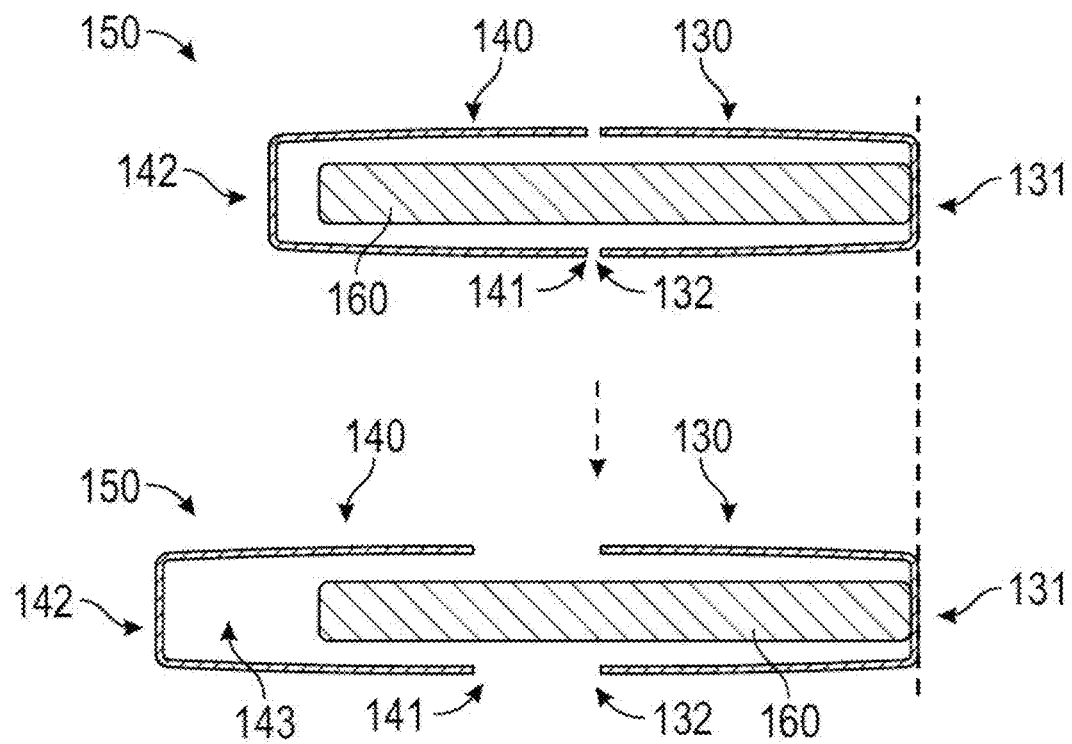

In other embodiments, the clot retrieval devices (100) described herein comprise an inner shaft (160) affixed to the first end (131; e.g., the proximal end) of the first support portion (130) (see FIG. 6B). This allows the second support portion (140) to be movable relative to the first support portion (130) and allows for the second lumen (143) of the second support portion (140) to slide over the inner shaft (160). In some embodiments, the first support portion (130) is stationary relative to the delivery shaft (110). In some embodiments, the first end (131) of the first support portion (130) is fixed to the distal delivery shaft end (111) of the delivery shaft (110). When the second support portion (140) slides distally along the inner shaft (160), away from the first support portion (130), the capturing basket (120) elongates (i.e., the second basket end (122) moves away (i.e., distally) from the first basket end (121)). Additionally, when the second support portion (140) slides proximally along the inner shaft (160), towards the first support portion (130), the capturing basket (120) collapses (i.e., the second basket end (122) moves towards (i.e., proximally) the first basket end (121)).

Figure 6C:
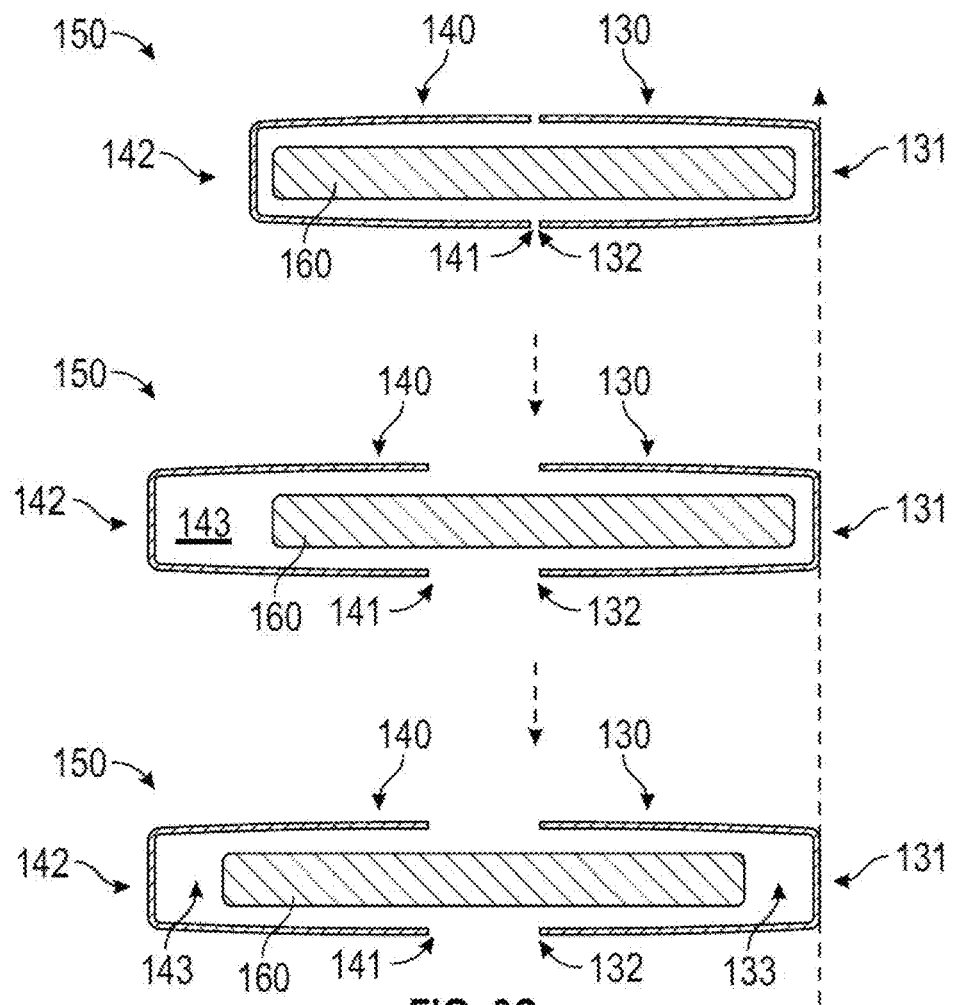

In certain embodiments, the clot retrieval devices (100) described herein comprise an inner shaft (160) that is free-floating and not affixed to either end (i.e., not affixed to the first end (131) of the first support portion (130) or to the second end (142) of the second support portion (140)) (see FIG. 6C). This allows the second support portion (140) to be movable relative to the first support portion (130). In some embodiments, the first support portion (130) is stationary relative to the delivery shaft (110). In some embodiments, the first end (131) of the first support portion (130) is fixed to the distal end (111) of the delivery shaft (110). In some embodiments, the second end (142) of the second support portion (140) is fixed to the second basket end (122) of the capturing basket (120). Using the inner shaft (160) as a guide (e.g., a structure that directs the motion or positioning of something), when the second support portion (140) moves away from the first support portion (130), the capturing basket (120) elongates (i.e., the second basket end (122) moves away (i.e., distally) from the first basket end (121)). Additionally, when the second support portion (140) slides proximally along the inner shaft (160), towards the first support portion (130), the capturing basket (120) collapses (i.e., the second basket end (122) moves towards (i.e., proximally) the first basket end (121)).

Figure 6D:
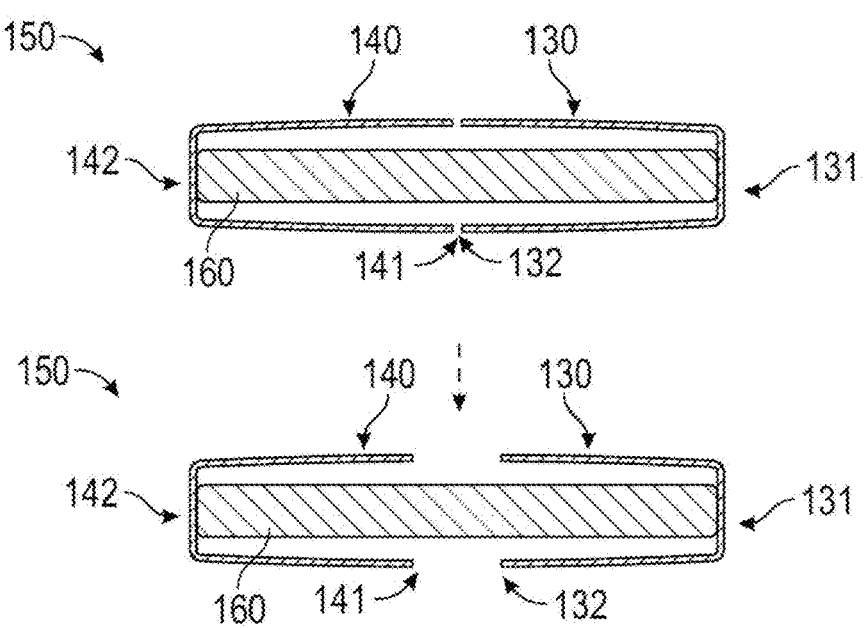

In further embodiments, the clot retrieval devices (100) described herein comprise an inner shaft (160) affixed to both the first end (131) of the first support portion (130) or to the second end (142) of the second support portion (140)) (see FIG. 6D). In this embodiment, the inner shaft (160) is extendable and may be made from an elastomeric material. When the length of the inner shaft (160) increases (i.e., the inner shaft (160) is stretched) the second basket end (122) moves away (i.e., distally) from the first basket end (121) thus elongating the capturing basket (120). Additionally, when the length of the inner shaft (160) decreases (i.e., the inner shaft (160) is contracted (e.g., shortened)) the second basket end (122) moves towards (i.e., proximally) the first basket end (121)) thus collapsing the capturing basket (120).

In certain embodiments, the support component (150) comprises a telescoping shaft. In some embodiments, when the telescoping shaft of the support component (150) is extended, the capturing basket (120) elongates. In some embodiments, the telescoping shaft of the support component (150) is shortened, and the capturing basket (120) collapses.

In some embodiments, the support component (150) has flexibility or elasticity. In some embodiments, the support component (150) is made of a flexible or elastic material. Such flexible or elastic material may include but is not limited to a polyether ether ketone (PEEK) polymer comprising a polytetrafluoroethylene (PTFE) coating. In certain embodiments, the support component (150) comprises material of optimum flexibility such as PEEK/PTFE composite. Other flexible/elastic materials may be used in accordance with the present device (e.g., the support component (150).

In some embodiments, the capturing basket (120) has a length of 30 mm to 50 mm. In other embodiments, the capturing basket (120) has a length of about 20 mm to 60 mm, or about 20 mm to 50 mm, or about 20 mm to 40 mm, or about 20 mm to 30 mm, or about 30 mm to 60 mm, or about 30 mm to 50 mm, or about 30 mm to 40 mm, or about 40 mm to 60 mm, or about 40 mm to 50 mm, or about 50 mm to 60 mm. In further embodiments, the capturing basket (120) has a length of about 20 mm, or about 30 mm, or about 40 mm, or about 50 mm, or about 60 mm.

In some embodiments, the capturing basket (120) may elongate (e.g., the second basket end (122) moves away (i.e., distally) from the first basket end (121)) or collapse (e.g., the second basket end (122) moves towards (i.e., proximally) the first basket end (121)) by about 20% of the original length of the capturing basket (120). In other embodiments, the capturing basket (120) may elongate or collapse by about 10% of the original length of the capturing basket (120). In further embodiments, the capturing basket (120) may elongate or collapse by about 30% of the original length of the capturing basket (120).

In some embodiments, the capturing basket (120) may elongate or collapse by 5 mm to 10 mm. In other embodiments, the capturing basket (120) may elongate or collapse by about 2 mm to 18 mm, or about 2 mm to 16 mm, or about 2 mm to 14 mm, or about 2 mm to 12 mm, or about 2 mm to 10 mm, or about 2 mm to 8 mm, or about 2 mm to 6 mm or about 2 mm to 4 mm, or about 4 mm to 18 mm, or about 4 mm to 16 mm, or about 4 mm to 14 mm, or about 4 mm to 12 mm, or about 4 mm to 10 mm, or about 4 mm to 8 mm, or about 4 mm to 6 mm or about 6 mm to 18 mm, or about 6 mm to 16 mm, or about 6 mm to 14 mm, or about 6 mm to 12 mm, or about 6 mm to 10 mm, or about 6 mm to 8 mm or about 8 mm to 18 mm, or about 8 mm to 16 mm, or about 8 mm to 14 mm, or about 8 mm to 12 mm, or about 8 mm to 10 mm, or about 10 mm to 18 mm, or about 10 mm to 16 mm, or about 10 mm to 14 mm, or about 10 mm to 12 mm, or about 12 mm to 18 mm, or about 12 mm to 16 mm, or about 12 mm to 14 mm, or about 14 mm to 18 mm, or about 14 mm to 16 mm, or about 16 mm to 18 mm.

In some embodiments, the capturing basket (120) may have an unconstrained (i.e., fully expanded) diameter of 10 mm to 14 mm. In other embodiments, the capturing basket (120) may have an unconstrained (i.e., fully expanded) diameter of about 6 mm to 18 mm, or about 6 mm to 16 mm, or about 6 mm to 14 mm, or about 6 mm to 12 mm, or about 6 mm to 10 mm, 6 mm to 8 mm, or about 8 mm to 18, or about 8 mm to 16 mm, or about 8 mm to 14 mm, or about 8 mm to 12 mm, or about 8 mm to 10 mm, or about 10 mm to 18, or about 10 mm to 16 mm, or about 10 mm to 14 mm, or about 10 mm to 12 mm, or about 12 mm to 18, or about 12 mm to 16 mm, or about 12 mm to 14 mm, or about 14 mm to 18, or about 14 mm to 16 mm, or about 16 mm to 18 mm. In further embodiments, the capturing basket (120)

may have an unconstrained (i.e., fully expanded) diameter of 6 mm or 8 mm, or 10 mm, or 12 mm, or 14 mm, or 16 mm, or 18 mm.

In some embodiments, the capturing basket (120) has an unconstrained (i.e., fully expanded) diameter that has a constant diameter along the mid-portion of its length. For example, the capturing basket (120) may resemble a cylinder or tube (see FIG. 5). In other embodiments, the capturing basket (120) has an unconstrained (i.e., fully expanded) diameter comprising a continuous taper such that the first basket end (121) has a larger diameter compared to the second basket end (122) (see FIG. 5; i.e., the second basket end (122) has a smaller diameter compared to the first basket end (121)). Without wishing to limit the present invention to any theories or mechanisms it is believed that the smaller diameter at the second basket end (122) enables the capturing basket (120) to enter smaller diameter distal vessels whereas the larger diameter at the first basket end (121) enables the capturing basket (120) to be effective at proximally larger diameter vessels. In some embodiments, the capturing basket (120) may be able to retrieve clots from two vessels at the same time such that the distal vessel is a branch vessel of the proximal vessel.

In some embodiments, the capturing basket (125) may have a constrained (i.e., compressed) diameter of 1.5 mm to 4.0 mm. In other embodiments, the capturing basket (125) may have a constrained (i.e., compressed) of about 1.0 mm to 4.5 mm, or about 1.0 mm to 4.0 mm, or about 1.0 mm to 3.5 mm or about 1.0 mm to 3.0 mm, or about 1.0 mm to 2.5 mm, or about 1.0 mm to 2.0 mm, or about 1.0 mm to 1.5 mm, or about 1.5 mm to 4.5 mm, or about 1.5 mm to 4.0 mm, or about 1.5 mm to 3.5 mm or about 1.5 mm to 3.0 mm, or about 1.5 mm to 2.5 mm, or about 1.5 mm to 2.0 mm, or about 2.0 mm to 4.5 mm, or about 2.0 mm to 4.0 mm, or about 2.0 mm to 3.5 mm or about 2.0 mm to 3.0 mm, or about 2.0 mm to 2.5 mm, or about 2.5 mm to 4.5 mm, or about 2.5 mm to 4.0 mm, or about 2.5 mm to 3.5 mm or about 2.5 mm to 3.0 mm, or about 3.0 mm to 4.5 mm, or about 3.0 mm to 4.0 mm, or about 3.0 mm to 3.5 mm or about 3.5 mm to 4.5 mm, or about 3.5 mm to 4.0 mm, or about 4.0 mm to 4.5 mm.

The capturing basket (120) is loaded in its constrained (i.e., compressed) state into a fixed diameter catheter. In some embodiments, the capturing basket (120) has a constrained (i.e., compressed) diameter that has a constant diameter along the mid-portion of its length (i.e., the constrained (i.e., compressed) diameter is not tapered).

In preferred embodiments, the cells (123) are closed cells. In other embodiments, the cells (123) are opened cells. As used herein, a "closed cell" refers to a cell that is fully enclosed and defined by struts.

The capturing basket (125) may further include cells (123) that decrease in size from a middle portion of the capturing basket towards the first basket end (121) and the second basket end (122). In some embodiments, the cells (123) at the second basket end (122; i.e., the distal end) of the capturing basket (120) are smaller in size than the cells (123) in the middle of the capturing basket (120) and at the first end (121) of the capturing basket (120). In some embodiments, the cells in the middle of the capturing basket (120) are the largest (e.g., when compared to cells (123) at the first end (121) or the second end (122)). In some embodiments, the cells (123) of the capturing basket (120) are all equal in size.

Without wishing to limit the present invention to any theory or mechanism it is believed that the smaller cells (123) at the second basket end (122; i.e., the distal end) of the capturing basket (120) acts as a secondary capture "device" for clots that get dislodged from the device or get broken into smaller pieces.

In some embodiments, the cells (123) are quadrilateral in shape. In other embodiments, the cells (123) are irregular quadrilaterals in shape. As used herein, an "irregular quadrilateral" refers to quadrilaterals that are symmetrical but are not required to have congruent sides or angles. In other embodiments, the cells (123) are rhombus in shape. In some embodiments, the cells (123) are diamond-shaped. As used herein, a "diamond-shaped" and "rhombus" may be used interchangeably and refer to a quadrilateral with four straight, equal sides with both pairs of opposite sides being parallel. In some embodiments, the cells (123) are kite-shaped. As used herein, a "kite-shaped" refers to a quadrilateral whose four sides can be grouped into two pairs of equal-length sides that are adjacent to each other.

In some embodiments, the cells (123) at the first basket end (121) are kite-shaped. In some embodiments, the cells (123) at the first basket end (121) are kite-shaped in which the longer sides are disposed towards the first basket end (121). Without wishing to limit the present invention to any theory or mechanism, it is believed that kite-shaped cells (123) at the first basket end (121) facilitates the retrieval of the clot retrieval device (100) described herein containing a clot (e.g., the embolus) into a catheter (e.g., an aspiration catheter).

In preferred embodiments, the cells (123) described herein have a height of 4 mm to 8 mm. In some embodiments, the cells (123) have a height of about 2 mm to 10 mm, or about 2 mm to 9 mm, or about 2 mm to 8 mm, or about 2 mm to 7 mm, or about 2 mm to 6 mm, or about 2 mm to 5 mm, or about 2 mm to 4 mm, or about 2 mm to 3 mm, or about 3 mm to 10 mm, or about 3 mm to 9 mm, or about 3 mm to 8 mm, or about 3 mm to 7 mm, or about 3 mm to 6 mm, or about 3 mm to 5 mm, or about 3 mm to 4 mm, or about 4 mm to 10 mm, or about 4 mm to 9 mm, or about 4 mm to 8 mm, or about 4 mm to 7 mm, or about 4 mm to 6 mm, or about 4 mm to 5 mm, or about 5 mm to 10 mm, or about 5 mm to 9 mm, or about 5 mm to 8 mm, or about 5 mm to 7 mm, or about 5 mm to 6 mm, or about 6 mm to 10 mm, or about 6 mm to 9 mm, or about 6 mm to 8 mm, or about 6 mm to 7 mm, or about 7 mm to 10 mm, or about 7 mm to 9 mm, or about 7 mm to 8 mm, or about 8 mm to 10 mm, or about 8 mm to 9 mm, or about 9 mm to 10 mm. In further embodiments, the cells (123) described herein have a height of about 2 mm, or 3 mm, or 4 mm, or 5 mm, or 6 mm, or 7 mm, or 8 mm, or 9 mm, or 10 mm.

In preferred embodiments, the cells (123) described herein have a length of 6 mm to 16 mm. In some embodiments, the cells (123) have a length of about 4 mm to 18 mm, or about 4 mm to 16 mm, or about 4 mm to 14 mm, or about 4 mm to 12 mm, or about 4 mm to 10 mm, or about 4 mm to 8 mm, or about 4 mm to 6 mm, or about 6 mm to 18 mm, or about 6 mm to 16 mm, or about 6 mm to 14 mm, or about 6 mm to 12 mm, or about 6 mm to 10 mm, or about 6 mm to 8 mm, or about 8 mm to 18 mm, or about 8 mm to 16 mm, or about 8 mm to 14 mm, or about 8 mm to 12 mm, or about 8 mm to 10 mm, or about 10 mm to 18 mm, or about 10 mm to 16 mm, or about 10 mm to 14 mm, or about 10 mm to 12 mm, or about 12 mm to 18 mm, or about 12 mm to 16 mm, or about 12 mm to 14 mm, or about 14 mm to 18 mm, or about 14 mm to 16 mm, or about 16 mm to 18 mm. In further embodiments, the cells (123) described herein have a length of about 4 mm, or 6 mm, or 8 mm, or 10 mm, or 12 mm, or 14 mm, or 16 mm, or 18 mm.

In some embodiments, the plurality of cells (123) defined by struts (124) exerts an outward radial force. Generally, a radial force is defined as a force exerted in a radial direction towards the center or away from the center. As used herein, an "outward radial force" may refer to a force exerted outward (i.e., away from the center) by the capturing basket (120) when it is compressed to 50% of its unconstrained diameter.

In preferred embodiments, the outward radial force is 0.10 N/mm length to 0.15 N/mm length. In some embodiments, the outward radial force is about 0.05 N/mm length to 0.20 N/mm length, or about 0.05 N/mm length to 0.18 N/mm length, or about 0.05 N/mm length to 0.16 N/mm length, or about 0.05 N/mm length to 0.15 N/mm length, or about 0.05 N/mm length to 0.14 N/mm length, or about 0.05 N/mm length to 0.12 N/mm length, or about 0.05 N/mm length to 0.10 N/mm length, or about 0.05 N/mm length to 0.08 N/mm length, or about 0.05 N/mm length to 0.06 N/mm length, or about 0.06 N/mm length to 0.20 N/mm length, or about 0.06 N/mm length to 0.18 N/mm length, or about 0.06 N/mm length to 0.16 N/mm length, or about 0.06 N/mm length to 0.15 N/mm length, or about 0.06 N/mm length to 0.14 N/mm length, or about 0.06 N/mm length to 0.12 N/mm length, or about 0.06 N/mm length to 0.10 N/mm length, or about 0.06 N/mm length to 0.08 N/mm length, or about 0.08 N/mm length to 0.20 N/mm length, or about 0.08 N/mm length to 0.18 N/mm length, or about 0.08 N/mm length to 0.16 N/mm length, or about 0.08 N/mm length to 0.15 N/mm length, or about 0.08 N/mm length to 0.14 N/mm length, or about 0.08 N/mm length to 0.12 N/mm length, or about 0.08 N/mm length to 0.10 N/mm length, or about 0.10 N/mm length to 0.20 N/mm length, or about 0.10 N/mm length to 0.18 N/mm length, or about 0.10 N/mm length to 0.16 N/mm length, or about 0.10 N/mm length to 0.15 N/mm length, or about 0.10 N/mm length to 0.14 N/mm length, or about 0.10 N/mm length to 0.12 N/mm length, or about 0.12 N/mm length to 0.20 N/mm length, or about 0.12 N/mm length to 0.18 N/mm length, or about 0.12 N/mm length to 0.16 N/mm length, or about 0.12 N/mm length to 0.15 N/mm length, or about 0.12 N/mm length to 0.14 N/mm length, or about 0.14 N/mm length to 0.20 N/mm length, or about 0.14 N/mm length to 0.18 N/mm length, or about 0.14 N/mm length to 0.16 N/mm length, or about 0.14 N/mm length to 0.15 N/mm length, or about 0.16 N/mm length to 0.20 N/mm length, or about 0.16 N/mm length to 0.18 N/mm length, or about 0.18 N/mm length to 0.20 N/mm length. In further embodiments, outward radial force is about 0.05 N/mm length, or about 0.06 N/mm length, or about 0.08 N/mm length, or about 0.10 N/mm length, or about 0.12 N/mm length, or about 0.14 N/mm length, or about 0.15 N/mm length, or about 0.16 N/mm length, or about 0.18 N/mm length, or about 0.20 N/mm length.

In some embodiments, the plurality of cells (123) defined by struts allows the embolus to ingress into the capturing basket (120). Without wishing to limit the present invention to any theory or mechanism it is believed that the shape and dimensions of the plurality of cells (123) defined by struts (124) as well as the width and thickness of said struts (124) allow an embolus to ingress into the capturing basket (120).

In preferred embodiments, the struts (124) have a width of 0.007 in to 0.010 in. As used herein, "width" refers to the measurement taken between two lateral sides of the strut (see FIG. 4; i.e., the measurement taken parallel to the support component (150)). In some embodiments, the struts (124) have a width of about 0.005 in to 0.014 in, or about 0.005 in to 0.013 in, or about 0.005 in to 0.012 in, or about 0.005 in to 0.011 in, or about 0.005 in to 0.010 in, or about 0.005 in to 0.009 in, or about 0.005 in to 0.008 in, or about 0.005 in to 0.007 in, or about 0.005 in to 0.006 in, or about 0.006 in to 0.014 in, or about 0.006 in to 0.013 in, or about 0.006 in to 0.012 in, or about 0.006 in to 0.011 in, or about 0.006 in to 0.010 in, or about 0.006 in to 0.009 in, or about 0.006 in to 0.008 in, or about 0.006 in to 0.007 in, or about 0.007 in to 0.014 in, or about 0.007 in to 0.013 in, or about 0.007 in to 0.012 in, or about 0.007 in to 0.011 in, or about 0.007 in to 0.010 in, or about 0.007 in to 0.009 in, or about 0.007 in to 0.008 in, or about 0.008 in to 0.014 in, or about 0.008 in to 0.013 in, or about 0.008 in to 0.012 in, or about 0.008 in to 0.011 in, or about 0.008 in to 0.010 in, or about 0.008 in to 0.009 in, or about 0.009 in to 0.014 in, or about 0.009 in to 0.013 in, or about 0.009 in to 0.012 in, or about 0.009 in to 0.011 in, or about 0.009 in to 0.010 in, or about 0.010 in to 0.014 in, or about 0.010 in to 0.013 in, or about 0.010 in to 0.012 in, or about 0.010 in to 0.011 in, or about 0.011 in to 0.014 in, or about 0.011 in to 0.013 in, or about 0.011 in to 0.012 in, or about 0.012 in to 0.014 in, or about 0.012 in to 0.013 in, or about 0.013 in to 0.014 in.

In preferred embodiments, the struts (124) have a thickness of 0.007 in to 0.010 in. As used herein, "thickness" refers to the measurement taken from an outer surface of the strut to an inner surface of the strut (see FIG. 4; i.e., the measurement taken perpendicular to the support component (150)). In some embodiments, the struts (124) have a thickness of about 0.005 in to 0.014 in, or about 0.005 in to 0.013 in, or about 0.005 in to 0.012 in, or about 0.005 in to 0.011 in, or about 0.005 in to 0.010 in, or about 0.005 in to 0.009 in, or about 0.005 in to 0.008 in, or about 0.005 in to 0.007 in, or about 0.005 in to 0.006 in, or about 0.006 in to 0.014 in, or about 0.006 in to 0.013 in, or about 0.006 in to 0.012 in, or about 0.006 in to 0.011 in, or about 0.006 in to 0.010 in, or about 0.006 in to 0.009 in, or about 0.006 in to 0.008 in, or about 0.006 in to 0.007 in, or about 0.007 in to 0.014 in, or about 0.007 in to 0.013 in, or about 0.007 in to 0.012 in, or about 0.007 in to 0.011 in, or about 0.007 in to 0.010 in, or about 0.007 in to 0.009 in, or about 0.007 in to 0.008 in, or about 0.008 in to 0.014 in, or about 0.008 in to 0.013 in, or about 0.008 in to 0.012 in, or about 0.008 in to 0.011 in, or about 0.008 in to 0.010 in, or about 0.008 in to 0.009 in, or about 0.009 in to 0.014 in, or about 0.009 in to 0.013 in, or about 0.009 in to 0.012 in, or about 0.009 in to 0.011 in, or about 0.009 in to 0.010 in, or about 0.010 in to 0.014 in, or about 0.010 in to 0.013 in, or about 0.010 in to 0.012 in, or about 0.010 in to 0.011 in, or about 0.011 in to 0.014 in, or about 0.011 in to 0.013 in, or about 0.011 in to 0.012 in, or about 0.012 in to 0.014 in, or about 0.012 in to 0.013 in, or about 0.013 in to 0.014 in.

In some embodiments, the ratio between the width and thickness of the struts (124) may be at least 1.

The struts (124) as described herein may comprise surface heterogeneity. As used herein, "surface heterogeneity" refers to small (i.e., less than 0.5 mm) irregularities on a surface that makes said surface rough (i.e., not smooth). In some embodiments, the surface heterogeneity is on an inner surface of the struts (124). In other embodiments, the surface heterogeneity is on a lateral surface of the struts (124). In further embodiments, the surface heterogeneity is on an external surface of the struts (124). In some embodiments, the surface heterogeneity comprises grooves, protrusions, or a combination thereof. In certain embodiments, the protruding surface heterogeneity may be used as body markers (125), in which a radiopaque marker is added to the protrusion. In some embodiments, the surface heterogeneity on a surface of the struts (124) is made by using a laser (e.g., laser cutting) or other means.

Without wishing to limit the present invention to any theories or mechanisms, it is believed that the surface heterogeneity on the struts (124) described herein helps retain an embolus and keeps the embolus trapped (i.e., keeps the embolus retained) in the capturing basket (120). The surface heterogeneity may be prepared using laser or other means.

The whole capturing basket (120) may be made by laser cutting from a tube and shape-setting to a final shape. In various embodiments, the capturing basket (120) is made by layered deposition using 3D printing. Also, in various embodiments, vapor deposition can be employed to make the capturing basket.

Without wishing to limit the present invention to any theories or mechanisms it is believed that the use of a laser-cut capturing basket (120) is critical to the present invention because it enables the optimum radial force and cell sizes in the capturing basket (120) which allows for the capturing basket (120) to be able to dislodge clot from a vessel wall as well as to shear the clot before allowing it to ingress into the cell.

In some embodiments, the capturing basket (120) may comprise less metal which allows for more space for a clot to be retrieved through, thereby improving retrieval efficiency.

In some embodiments, the capturing basket (120) comprises at least six body markers (125). In other embodiments, the capturing basket (120) comprises at least eight body markers (125). In a further embodiment, the capturing basket (120) comprises at least ten body markers (125). In some embodiments, the capturing basket (120) comprises more than ten body markers (125).

Figure 1A:
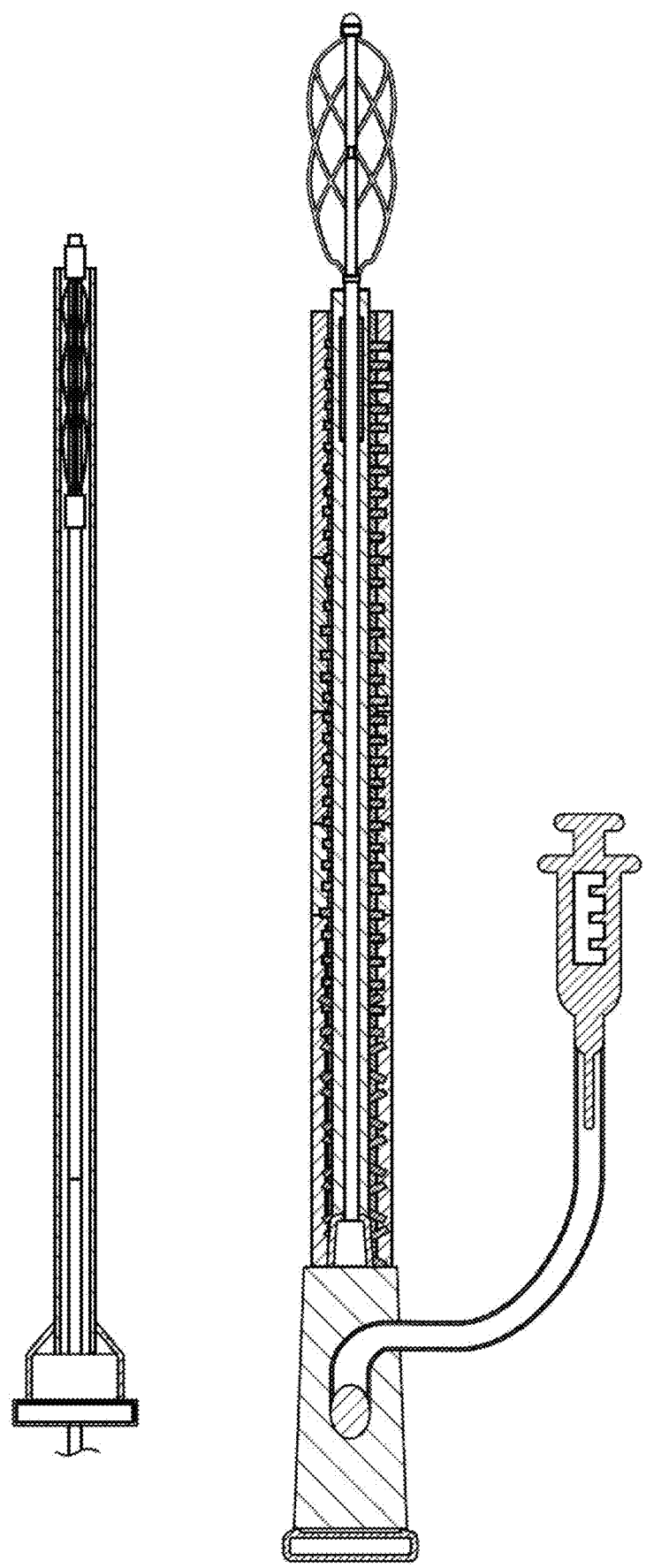
Figure 1B:
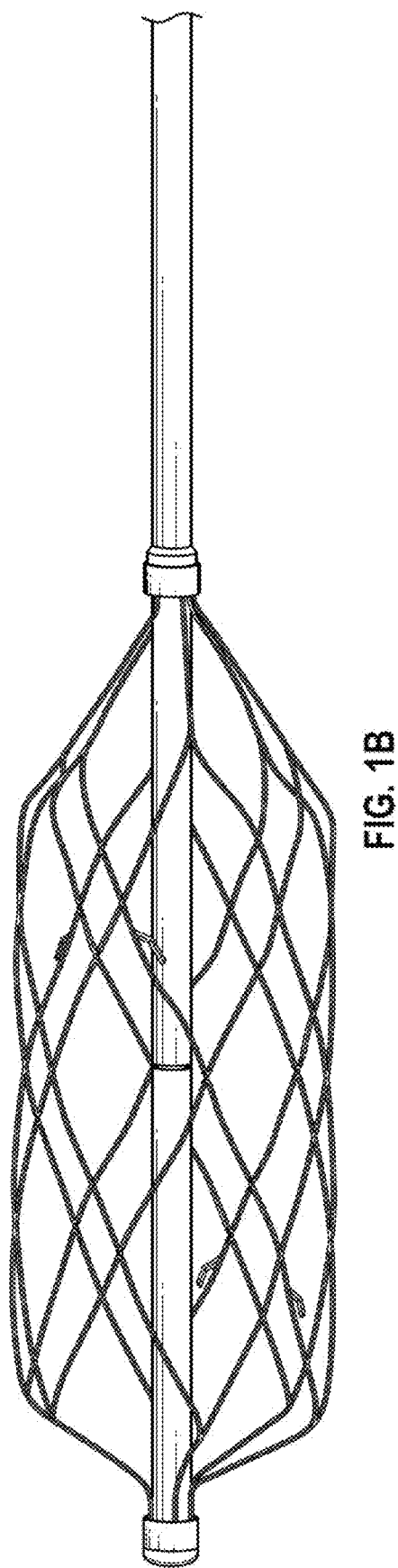
Figure 2:
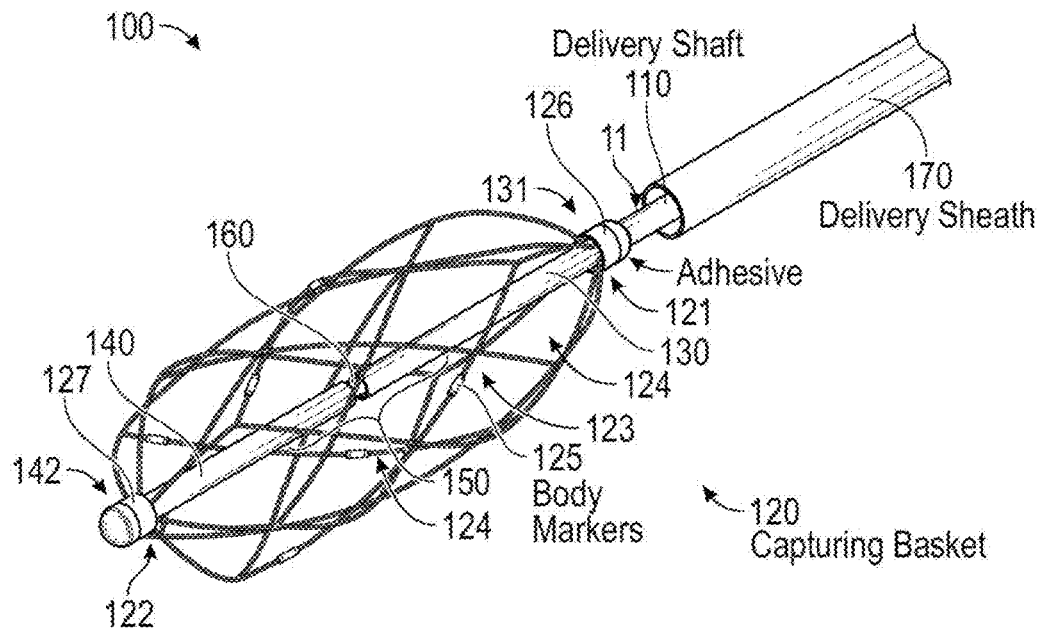
Figure 3A:
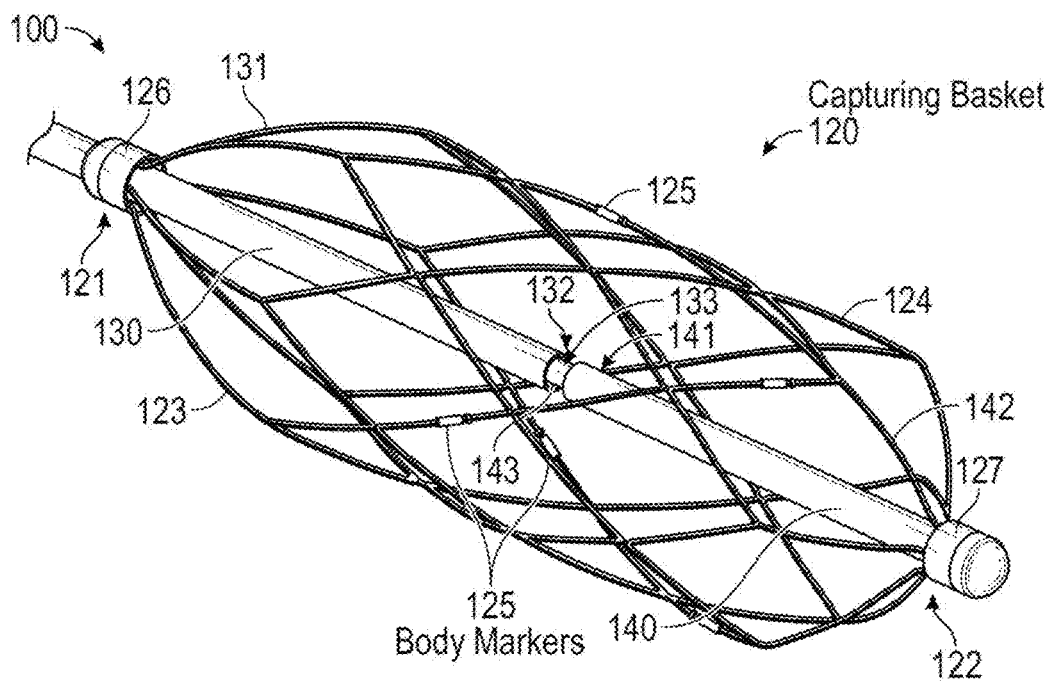
Figure 4:
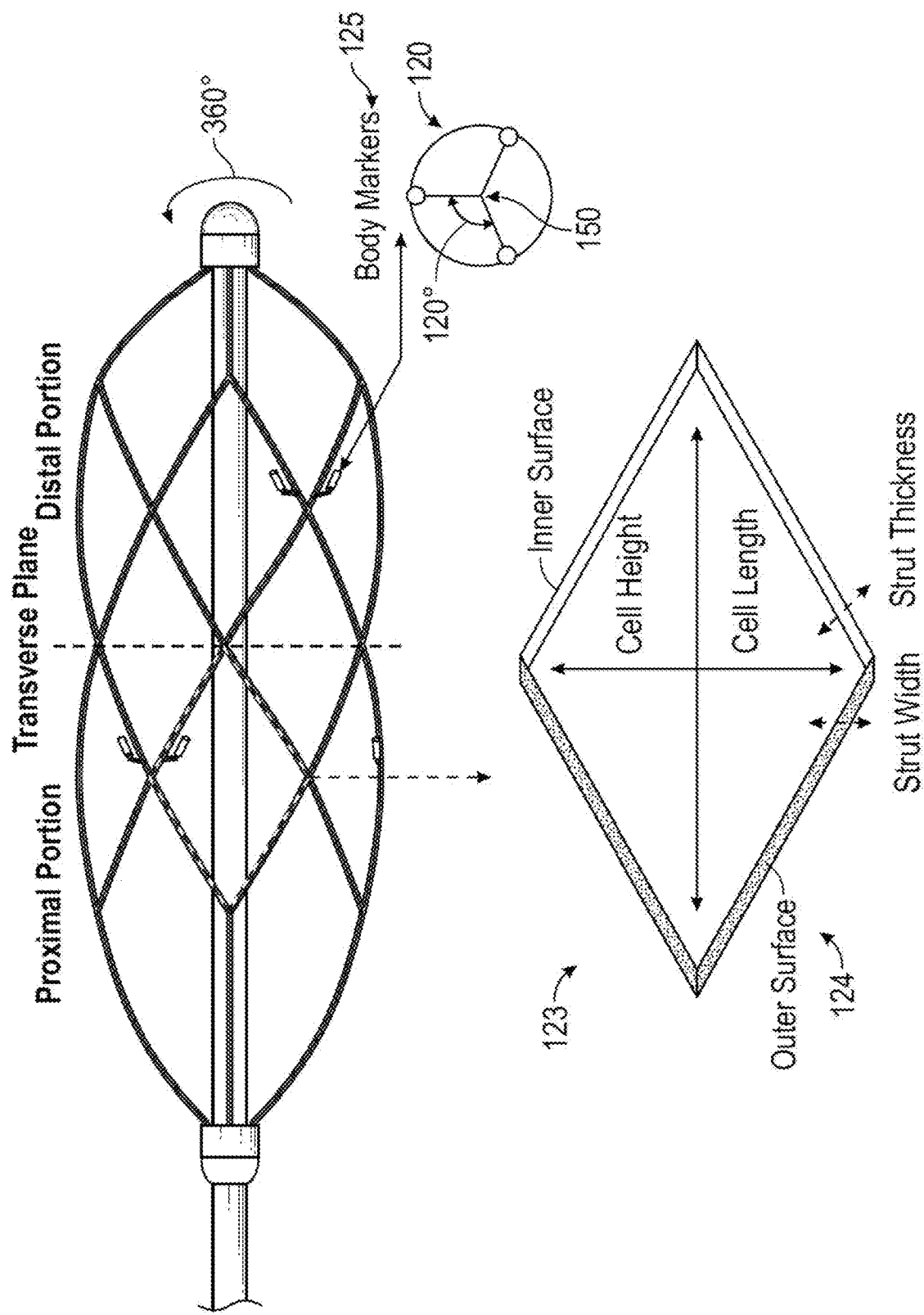
FIG. 4 shows how the clot retrieval device described herein may be divided into two portions (e.g., a distal portion or a proximal portion; top) and the dimensions of the cells (bottom).
Figure 5:
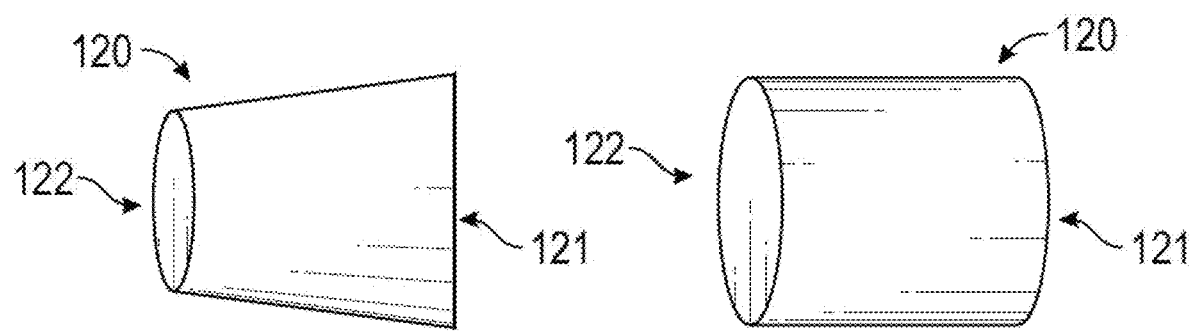
FIG. 5 shows an abstract diagram demonstrating a capturing basket comprising a tapered diameter (left) or a consistent diameter (right).

The capturing basket (120) may be divided along a transverse plane (e.g., divided perpendicular to the support structure (150); see FIG. 4). Dividing the capturing basket (120) along a transverse plane creates two portions (e.g., a distal portion and a proximal portion). In some embodiments, the body markers (125) are distributed equally between the two portions (e.g., a distal portion and a proximal portion) of the capturing basket (120) created by the transverse plane.

In some embodiments, the body markers (125) described herein are distributed equiangularly around the capturing basket (120). In some embodiments, the body markers (125) described herein are distributed equiangularly around the capturing basket (120) within a single portion (e.g., the distal portion or the proximal portion). In some embodiments, the body markers (125) within a single portion (e.g., the distal portion or the proximal portion) of the capturing basket are 120° apart from each other.

The body markers (125) described herein are disposed on the struts (124) of the capturing basket (120). In some embodiments, the body markers (125) are aligned with the struts (124) of the capturing basket (120). In other embodiments, the body markers (125) are protruded from the struts (124) of the capturing basket (120). In some embodiments, the body markers (125) are radiopaque markers. In some embodiments, the radiopaque markers comprise tantalum, platinum, or other radiopaque materials.

Without wishing to limit the present invention to any theories or mechanisms, it is believed that the body markers described herein allow for visualization to be used as an aid to see when the clot is captured or lost and for enhanced clot retention during retrieval.

In some embodiments, the capturing basket (120) is configured to rotate. In some embodiments, the capturing basket (120) is configured to axially rotate. In some embodiments, the capturing basket (120) may be rotated bidirectionally. In some embodiments, the capturing basket (120) rotates at low revolutions per minute (rpm). The capturing basket may rotate at about 2 rpm to 10 rpm, or about 2 rpm to 8 rpm, or about 2 rpm to 6 rpm, or about 2 rpm to 4 rpm, or about 4 rpm to 10 rpm, or about 4 rpm to 6 rpm, or about 6 rpm to 10 rpm, or about 6 rpm to 8 rpm, or about 8 rpm to 10 rpm.

In order to remove large clots, it can sometimes be helpful to shear them into smaller pieces without causing uncontrolled embolic debris (e.g., debris that is dislodged and travels to undesirable locations). Without wishing to limit the present invention to any theories or mechanisms, it is believed that rotating the capturing basket enables controlled shearing of the embolus and also helps dislodge the embolus from the vessel wall. As used herein, "controlled shearing" may refer to slicing (e.g., circumferentially slicing) an object (e.g., a clot) into chunks and does not refer to macerating or pulverizing (i.e., reducing to fine particles by crushing or grinding) an object (e.g., a clot).

The capturing basket (120) may be attached to a delivery shaft (i.e., the pusher or a push-wire; 110), which is a wire that delivers the capturing basket (120) through a vasculature to the location of an embolus and pushes the capturing basket (120) to the side of an embolus via a catheter.

In preferred embodiments, the delivery shaft (i.e., the pusher; 110) is braided. In certain embodiments, the delivery shaft (i.e., the pusher; 110) is hollow. In some embodiments, the delivery shaft (i.e., the pusher; 110) is hollow for at least a section of said shaft. In other embodiments, the delivery shaft (i.e., the pusher; 110) is hollow for the entire length of the delivery shaft (110). In further embodiments, the delivery shaft (i.e., the pusher; 110) comprises a hollow distal end. In certain embodiments, the delivery shaft (i.e., the pusher; 110) is solid.

The delivery shaft (i.e., the pusher; 110) may be rotated. In some embodiments, the delivery shaft (i.e., the pusher; 110) may be axially-rotated. In other embodiments, the delivery shaft (i.e., the pusher; 110) may be hand-rotated. In some embodiments, In some embodiments, the delivery shaft (i.e., the pusher; 110) is able to be rotated bidirectionally. In some embodiments, the delivery shaft (i.e., the pusher; 110) is able to withstand torque. In some embodiments, the delivery shaft (i.e., the pusher; 110) allows for torque transfer. In some embodiments, the delivery shaft (i.e., the pusher; 110) allows for a 1:1 torque transfer. For example, when a distal end of the delivery shaft (i.e., the pusher; 110) is rotated (e.g., hand-rotated), the equivalent torque is transferred through the delivery shaft (i.e., the pusher; 110) to the capturing basket (120), such that the capturing basket (120) is also rotated. In some embodiments, when the delivery shaft (110) is rotated, torque is transferred from the delivery shaft (110) to the capturing basket (120), such that the capturing basket (120) is also rotated.

In certain embodiments, the delivery shaft (i.e., the pusher; 110) is able to withstand low revolutions per minute (rpm). In certain embodiments, the delivery shaft (i.e., the pusher; 110) is able to withstand revolutions per minute (rpm) of about 2 to 10 rpm. In other embodiments, the delivery shaft (i.e., the pusher; 110) is able to withstand rotations per minute (rpm) of about 2 to 10 rpm, or about 2 to 8 rpm, or about 2 to 6 rpm, or about 2 to 4 rpm, or about 4 to 10 rpm, or about 4 to 6 rpm, or about 6 to 10 rpm, or about 6 to 8 rpm, or about 8 to 10 rpm.

In some embodiments, the devices described herein further comprise a first marker (126) and a second marker (127). In some embodiments, the first marker (126) is disposed at the first basket end (121), and the second marker (127) is disposed at the second basket end (122). In certain embodiments, the first marker (126) and the second marker (127) are radiopaque markers. The radiopaque markers may be positioned to reveal the clot under fluoroscopy. In some embodiments, the radiopaque markers comprise tantalum, platinum, or other radiopaque materials.

For enhanced radiopacity and visualization, radiopaque markers made of tantalum, platinum, or other radiopaque materials may be installed into various portions of the capturing basket.

In some embodiments, the radiopaque markers described herein may be textured to impart additional embolus retention. The textured radiopaque markers may be located in multiple radial directions around the capturing basket (120) to retain dislodged pieces of an embolus in any portion of the capturing basket.

In some embodiments, the device is rotatable. In other embodiments, the device is configured to rotate. For example, when a distal end of the delivery shaft (i.e., the pusher; 110) is rotated, torque is transferred through the delivery shaft (110) to the capturing basket (120), such that the capturing basket (120) is also rotated. In some embodiments, the device is axially rotated. In some embodiments, the device is hand-rotated. In some embodiments, the device may be rotated bidirectionally.

In certain embodiments, the device (100) is able to withstand low revolutions per minute (rpm). In certain embodiments, the device (100) is able to withstand rotations per minute (rpm) of about 2 to 10 rpm. In other embodiments, the device (100) is able to withstand rotations per minute (rpm) of about 2 to 10 rpm, or about 2 to 8 rpm, or about 2 to 6 rpm, or about 2 to 4 rpm, or about 4 to 10 rpm, or about 4 to 6 rpm, or about 6 to 10 rpm, or about 6 to 8 rpm, or about 8 to 10 rpm.

Without wishing to limit the present invention to any theories or mechanisms, it is believed that rotating the device at low rpms prevents red blood cells (RBC) from being hemolyzed and also prevents tachycardia. Both of which may occur when using a high rpm device.

In some embodiments, the devices described herein further comprise a delivery sheath (170). In some embodiments, the clot retrieval device (100) is loaded into the delivery sheath (170) before delivery. In some embodiments, the delivery sheath (170) comprising the clot retrieval device (100) is pushed through a catheter (180; e.g., an aspiration catheter) to reach a target location (i.e., a target lesion; e.g., a clot). In some embodiments, the devices described herein further comprise a delivery catheter (180).

The devices described herein may further comprise a catheter (e.g., an aspiration catheter). Aspiration at a proximal end of the catheter, while the clot retrieval device (100) comprising a clot is being pulled into the catheter and out of the body, may increase the efficiency of clot retrieval. Aspiration can be accomplished manually or using a pump. The devices (100) described herein may operate with or without aspiration assistance In some embodiments, the delivery catheter (180) is an aspiration catheter. In some embodiments, the delivery catheter (180; e.g., the aspiration catheter) comprises a 24 Fr catheter, a 20 Fr catheter, a 16 Fr catheter, or a 12 Fr catheter. In other embodiments, the delivery catheter (180; e.g., the aspiration catheter) comprises a catheter of about 10 Fr to 26 Fr, or about 10 Fr to 24 Fr, or about 10 Fr to 22 Fr, or about 10 Fr to 20 Fr, or about 10 Fr to 18 Fr, or about 10 Fr to 16 Fr, or about 10 Fr to 14 Fr, or about 10 Fr to 12 Fr, or about 12 Fr to 26 Fr, or about 12 Fr to 24 Fr, or about 12 Fr to 22 Fr, or about 12 Fr to 20 Fr, or about 12 Fr to 18 Fr, or about 12 Fr to 16 Fr, or about 12 Fr to 14 Fr, or about 14 Fr to 26 Fr, or about 14 Fr to 24 Fr, or about 14 Fr to 22 Fr, or about 14 Fr to 20 Fr, or about 14 Fr to 18 Fr, or about 14 Fr to 16 Fr, or about 16 Fr to 26 Fr, or about 16 Fr to 24 Fr, or about 16 Fr to 22 Fr, or about 16 Fr to 20 Fr, or about 16 Fr to 18 Fr, or about 18 Fr to 26 Fr, or about 18 Fr to 24 Fr, or about 18 Fr to 22 Fr, or about 18 Fr to 20 Fr, or about 20 Fr to 26 Fr, or about 20 Fr to 24 Fr, or about 20 Fr to 22 Fr, or about 22 Fr to 26 Fr, or about 22 Fr to 24 Fr, or about 24 Fr to 26 Fr.

In some embodiments, the delivery catheter (180; e.g., the aspiration catheter) comprises an attached hub sub-assembly. In some embodiment, the delivery catheter (180; e.g., the aspiration catheter) comprises a valve. In some embodiments, the large size engineered valve in the proximal hub allows for high aspiration efficiency. For example, the valve enables the clot to be aspirated through a side port, while a main port can be opened and closed to the desired opening diameter with the help of a rotating valve. The rotating valve may withstand aspiration forces and remain sealed around any device (e.g., the clot retrieval device (100)) inserted through it to enable aspiration through the side port.

In some embodiments, the delivery catheter (180; e.g., the aspiration catheter) comprises a syringe. In some embodiments, the syringe comprises a 60 cc Vac-Lok syringe or a 30 cc Vac-Lok syringe.

The capturing basket (120) may be configured to be delivered by a delivery catheter (180) from an upstream direction in the blood vessel. In some embodiments, a distal opening of the delivery catheter has one or more extrusions extending from an inner surface of the delivery catheter, and one or more extrusions have sharp edges. The capturing basket (120) may be configured to be delivered by a delivery catheter (180) from an upstream direction in the blood vessel prior to being retrieved by the delivery catheter (180) where the distal opening of the delivery catheter (180) is configured to increase in size to retrieve the capturing basket (120).

In some embodiments, the distal opening of the delivery catheter (180) may have one or more extrusions extending from an inner surface of the delivery catheter (180) where the one or more extrusions have sharp edges and the one or more extrusions are retractable and the one or more extrusions with sharp edges are configured to shear the clot as the capturing basket (120) is retrieved by the distal end of the delivery catheter (180). The delivery catheter (180) may have one or more slits at the distal opening of the delivery catheter (180), where the distal opening of the delivery catheter (180) is configured to increase in size to retrieve the capturing basket.

The clot retrieval device (100) may further include a balloon catheter located near the distal opening of the delivery catheter (180) that has a funnel shape when inflated. The balloon catheter may have pores that, when the balloon catheter is inflated, allow blood to flow through the balloon catheter and prevent large blood clots from flowing through the balloon catheter. The proximal end of the delivery catheter (180) may be configured to be aspirated to aid in the retrieval of the capturing basket into the distal end of the delivery catheter.

The catheter may include a balloon that, when inflated, increases the opening of the distal end of the catheter. The balloon may have a funnel shape, which facilitates retrieval of the capturing basket into the catheter after the capturing basket traps an embolus. The balloon may further include a grid structure where the open areas of the balloon allow blood to pass through the balloon when the balloon is inflated. In various embodiments, the balloon is not limited to a funnel shape. The balloon may be in various shapes, such as a disc or a cylinder. External aspiration may be used on the apparatus to aid in retrieving an embolus.

In one embodiment, aspiration of the proximal end of the catheter may be used to increase the efficiency of embolus removal. The aspiration may be performed while the embolus is trapped within the capturing basket and being pulled into the catheter. In various embodiments, aspiration is not used to retrieve emboli.

In some embodiments, the present invention features a method of removing a clot. The method comprises loading the clot retrieval device (100) into a delivery sheath (170). The delivery sheath (170) is then pushed inside a pre-delivered catheter (180; e.g., an aspiration catheter). Once the clot retrieval device (100) reaches the target lesion, the delivery sheath (170) is withdrawn (i.e., withdrawn from the body). The clot retrieval device (100), more specifically the capturing basket (120), may help to break the clot from the vessel wall, if necessary. For example, the capturing basket (120) may be rotated (at low rpm such as 2-10 rpm) to dislodge the clot from the vessel wall. The capturing basket (120) may then be used to capture the clot and bring the clot near the tip of the catheter (180; e.g., the aspiration catheter). In some embodiments, aspiration, and retrieval of the clot via the capturing basket (120) work together to remove the clot from the lesion and outside of the body.

The present invention may feature a method of capturing a clot. The method comprises deploying a clot retrieval device (100) as described herein and expanding the capturing basket (120) on a side of the clot, between a vessel wall and the clot. In some embodiments, expanding the capturing basket (120) of the clot retrieval device (100) allows for the clot to ingress laterally into the capturing basket (120) of the clot retrieval device (100), thus capturing the clot. In some embodiments, the clot comprises an embolus.

The present invention may also feature a method of retaining a clot. The method comprises capturing the clot in a clot retrieval device (100) as described herein and visualizing and monitoring a distance between the body markers (125) on a portion of the capturing basket (120). In some embodiments, when the distance of the body markers (125) on the portion of the capturing basket (120) are stationary, the clot is retained in the capturing basket (120), and when the distance of the body markers (125), the portion of the capturing basket (120) changes the clot is escaping. In some embodiments, the clot comprises an embolus.

The present invention may further feature a method of capturing and retaining a clot. The method comprises deploying a clot retrieval device (100) as described herein on a side of the clot. In some embodiments, the method comprises expanding the capturing basket (120) on a side of the clot, between a vessel wall and the clot. In some embodiments, expanding the capturing basket (120) of the clot retrieval device (100) allows for the clot to ingress laterally into the capturing basket (120) of the clot retrieval device (100), thus capturing the clot. The method may further comprise visualizing and monitoring a distance between the body markers (125) on a portion of the capturing basket (120). In some embodiments, when the distance of the body markers (125) on the portion of the capturing basket (120) are stationary, the clot is retained in the capturing basket (120), and when the distance of the body markers (125), the portion of the capturing basket (120) changes the clot is escaping. In some embodiments, the clot comprises an embolus. In some embodiments, the distance of the body markers (125) on the portion of the capturing basket (120) increases. In other embodiments, the distance of the body markers (125) on the portion of the capturing basket (120) decreases.

In some embodiments, the distance of the body markers (125) on a singular portion (e.g., a distal portion or a proximal portion) of the capturing basket (120) increases. For example, if the clot is moving from the outside of the capturing basket (120) into the capturing basket (120) then the distance between the body markers (125) may increase. In some embodiments, the distance of the body markers (125) on a singular portion (e.g., a distal portion or a proximal portion) of the capturing basket (120) decreases. For example, if the clot is moving inside the capturing basket (120) to the outside of the capturing basket (120) then the distance between the body markers (125) may decrease.

In some embodiments, the distance of the body marker (125) within each of the two portions (e.g., a distal portion or a proximal portion) of the capturing basket (120) both increase. In some embodiments, the distance of the body marker (125) within each of the two portions (e.g., a distal portion or a proximal portion) of the capturing basket (120) both decrease. In certain embodiments, the distance of the body markers (125) within each of the two portions (e.g., a distal portion or a proximal portion) change independently from one another.

The present invention may feature a method of indirectly visualizing a captured clot. The method comprises capturing the clot with a capturing basket (120) as described herein and monitoring a distance between the body markers (125) on a portion of the capturing basket (120). In some embodiments, when the distance of the body markers (125) on the portion of the capturing basket (120) is stationary, the clot is captured and retained in the capturing basket (120), and when the distance of the body markers (125) the portion of the capturing basket (120) changes the clot lost from the capturing basket (120).

In some embodiments, while the above-mentioned invention (e.g., the devices described herein) is intended for treating pulmonary embolism, the devices described herein, in their entirety or partiality, are applicable to treating other peripheral vascular diseases including, but not limited to, deep vein thrombosis (DVT) or peripheral arterial clots.

EXAMPLE

The following is a non-limiting example of the present invention. It is to be understood that said example is not intended to limit the present invention in any way. Equivalents or substitutes are within the scope of the present invention.

A common medical condition is a pulmonary embolism, where an embolus gets trapped in the pulmonary artery. Most emboli form within veins deep in the body, such as in the legs. The formed embolus may travel from the legs through the inferior vena cava to the right atrium and right ventricle of the heart. The embolus may travel from the right ventricle to the pulmonary artery. The pulmonary artery bifurcates into a right pulmonary artery and a left pulmonary artery. The right pulmonary artery and left pulmonary artery continually bifurcate further into the lungs to oxygenate the blood. As the right pulmonary artery and left pulmonary artery branch, they become continually smaller, such that the embolus traveling through them may become stuck or lodged and inhibit or reduce blood flow downstream from the embolus. The devices (100) described herein are pushed through the pulmonary artery and delivered to the site of the embolus. The clot retrieval device (100) may trap the embolus so the embolus can be retrieved from the body.

Example 1: Use of a Clot Retrieval Device to Trap and Remove an Embolus from a Body A surgeon uses a guidewire to guide a catheter (180; e.g., an aspiration catheter) towards an embolus through the vasculature of a patient. The surgeon then loads a delivery sheath (170) comprising a clot retrieval device (100) into the pre-delivered catheter (180; e.g., an aspiration catheter) and pushes the delivery sheath (170) through said catheter (180). Once the delivery sheath (170) comprising a clot retrieval device (100) reaches the target lesion (e.g., the embolus), the surgeon is then able to push the clot retrieval device (100) from the distal end of the delivery sheath (170) using the delivery shaft (110). Once the clot retrieval device (100) is outside of the delivery sheath (170), the surgeon then withdraws the delivery sheath (170) from the body through the catheter (180). The capturing basket (120) expands once outside of the delivery sheath (170), allowing for the embolus to ingress laterally into the capturing basket (120) of the clot retrieval device (100), thus capturing the embolus. To ensure the embolus is fully dislodged from the vessel wall, the surgeon rotates the distal end of the delivery shaft (110) to rotate the capturing basket (120). Once the embolus is captured within the capturing basket (120), the surgeon uses the delivery shaft (110) to pull the capturing basket (120) towards the catheter (180). Using the body markers (125) disposed on the capturing basket (120), the surgeon monitors any changes in the distance of said marker. As the surgeon is pulling the delivery shaft (110), the distance between the body markers (125) on the capturing basket (120) begins to increase. To prevent loss of the embolus from the capturing basket (120), the surgeon slows down the pulling of the capturing basket (120) via the delivery shaft (110). Once the distance of the body markers (125) on the capturing basket (120) is stationary, the surgeon knows the clot is captured and retained in the capturing basket (120) and thus pulls the delivery shaft (110) at the newly adjusted rate. Once the capturing basket (120) reaches the distal end of the catheter (180), the surgeon uses aspiration to help pull the embolus and/or the capturing basket (120) into the catheter (180). Once the capturing basket (120) and the embolus are within the catheter (180), the surgeon then removes the catheter from the body.

Embodiments

The following embodiments are intended to be illustrative only and not to be limiting in any way.

Embodiments Set A

Embodiment 1A: A capturing basket (120) for capturing an embolus, the capturing basket comprising: (a) a first basket end (121) and a second basket end (122), (b) a plurality of cells (123) defined by struts (124), the struts having strut ends that are connected to the first basket end (121) and the second basket end (122), and (c) at least four body markers (125) disposed on the capturing basket (120).

Embodiment 2A: The basket of embodiment 1A, wherein the diameter of the capturing basket (120) is 10 mm to 14 mm.

Embodiment 3A: The basket of embodiment 1A or embodiment 2A, wherein the diameter of the capturing basket (120) is tapered between the first basket end (121) and the second basket end (122).

Embodiment 4A: The basket of embodiment 3A, wherein the first basket end (121) comprises a larger diameter compared to the second basket end (122).

Embodiment 5A: The basket of any one of embodiments 1A-4A, wherein the cells (123) are closed cells.

Embodiment 6A: The basket of any one of embodiments 1A-5A, wherein the cells (123) are quadrilateral in shape.

Embodiment 7A: The basket of any one of embodiments 1A-6A, wherein the cells (123) are rhombus in shape.

Embodiment 8A: The basket of any one of embodiments 1A-7A, wherein the struts (124) comprise surface heterogeneity.

Embodiment 9A: The basket of any one of embodiments 1A-8A, wherein the surface heterogeneity is on an inner surface of the struts (124).

Embodiment 10A: The basket of any one of embodiments 1A-8A, wherein the surface heterogeneity is on a lateral surface of the struts (124).

Embodiment 11A: The basket of embodiment 9A or embodiment 10A, wherein the surface heterogeneity comprises grooves, protrusions, or a combination thereof.

Embodiment 12A: The basket of any one of embodiments 1A-11A, wherein the plurality of cells (123) defined by struts (124) exert an outward radial force.

Embodiment 13A: The basket of any one of embodiments 1A-12A, wherein the plurality of cells (123) defined by struts (124) allows the embolus to ingress into the capturing basket (120).

Embodiment 14A: The basket of any one of embodiments 1A-13A, wherein the capturing basket (120) comprises at least six body markers (125).

Embodiment 15A: The basket of any one of 1A-14A, wherein the capturing basket (120) comprises at least eight body markers (125).

Embodiment 16A: The basket of any one of embodiments 1A-15A, wherein the body markers (125) are distributed equally between two portions of the capturing basket (120) created by a transverse plane.

Embodiment 17A: The basket of embodiment 16A, wherein the two portions of the capturing basket (120) comprise a distal portion and a proximal portion.

Embodiment 18A: The basket of embodiment 17A, where the body markers (125) are evenly distributed around the distal portion and/or the proximal portion of the capturing basket (120).

Embodiment 19A: The basket of embodiment 18A, wherein the body markers (125) in the distal portion and/or the proximal portion of the capturing basket (120) are 120° apart from each other.

Embodiment 20A: The basket of any one of embodiments 1A-19A, wherein the body markers (125) are disposed on the struts (124) of the capturing basket (120).

Embodiment 21A: The basket of embodiment 20A, wherein the body markers (125) are aligned with the struts (124) of the capturing basket (120).

Embodiment 22A: The basket of embodiment 20A, wherein the body markers (125) are protruded from the struts (124) of the capturing basket (120).

Embodiment 23A: The basket of any one of embodiments 1A-22A, wherein the body markers (125) are radiopaque markers.

Embodiment 24A: The basket of any one of embodiments 1A-23A, wherein the capturing basket (120) is configured to rotate.

Embodiment 25A: The basket of any one of embodiments 1A-24A, wherein the capturing basket (120) rotates at low revolutions per minute (rpm).

Embodiment 26A: The basket of any one of embodiments 1A-25A, wherein the capturing basket (120) rotates at 2 to 10 rpm.

Embodiment 27A: The basket of any one of embodiments 1A-26A, wherein rotating the capturing basket (120) enables controlled shearing of the embolus.

Embodiment 28A: The basket of any one of embodiments 1A-27A, wherein rotating the capturing basket (120) dislodges the embolus from a vessel wall.

Embodiment 29A: The basket of any one of embodiments 1A-28A, wherein the capturing basket (120) is configured to retrieve embolus from two vessels at the same time.

Embodiments Set B

Embodiment 1B: A clot retrieval device (100) comprising: (a) a delivery shaft (110) having a distal delivery shaft end (111); (b) a capturing basket (120) coupled to the distal delivery shaft end (111), wherein the capturing basket (120) comprises a first basket end (121), a second basket end (122), a plurality of cells (123) defined by struts (124), the struts (124) having strut ends that are connected to the first basket end (121) and the second basket end (122), and at least four body markers (125) disposed on the capturing basket (120); and (c) a support component (150) coupled to the distal delivery shaft end (111) and disposed within the capturing basket (120).

Embodiment 2B: The device (100) of embodiment 1B, wherein the support component (150) comprises: (a) a first support portion (130) comprising a first end (131), a second end (132), and a first lumen (133), wherein the first end (131) of the first support portion (130) is disposed within the basket (120) proximal to the first basket end (121), and (b) a second support portion (140), comprising a first end (141), a second end (142), and a second lumen (143), wherein the second end (142) of the second support portion (140) is disposed within the basket (120) proximal to the second basket end (122).

Embodiment 3B: The device (100) of embodiment 2B, wherein the first support portion (130) is stationary relative to the distal delivery shaft end (111).

Embodiment 4B: The device (100) of embodiment 2B, wherein the support component (150) further comprises an inner shaft (160) disposed through the first lumen (133) of the first support portion (130) and the second lumen (143) of the second support portion (140).

Embodiment 5B: The device (100) of any one of embodiments 2B-4B, wherein the inner shaft (160) is affixed to the second end (142) of the second support portion (140).

Embodiment 6B: The device (100) of any one of embodiments 2B-5B, wherein the inner shaft (160) slides within the first lumen (133) of the first support portion (130).

Embodiment 7B: The device (100) of embodiment 6B, wherein when the inner shaft (160) slides distally within the first lumen (133) of the first support portion (130), away from the first end (131) of the support portion (130), the capturing basket (120) elongates.

Embodiment 8B: The device (100) of embodiment 6B, wherein when the inner shaft (160) slides proximally within the first lumen (133) of the first support portion (130), towards the first end (131) of the support portion (130), the capturing basket (120) collapses.

Embodiment 9B: The device (100) of embodiment 1B, wherein the support component (150) comprises a telescoping shaft.

Embodiment 10B: The device (100) of embodiment 9B, wherein when the telescoping shaft of the support component (150) is extended, the capturing basket (120) elongates.

Embodiment 11B: The device (100) of embodiment 9B, wherein when the telescoping shaft of the support component (150) is shortened, the capturing basket (120) collapses.

Embodiment 12B: The device (100) of any one of embodiments 1B-11B, wherein the support component (150) comprises flexibility.

Embodiment 13B: The device (100) of any one of embodiments 1B-12B, wherein the diameter of the capturing basket (120) is 10 mm to 14 mm.

Embodiment 14B: The device (100) of any one of embodiments 1B-13B, wherein the diameter of the capturing basket (120) is tapered between the first basket end (121) and the second basket end (122).

Embodiment 15B: The device of embodiment 14B, wherein the first basket end (121) comprises a larger diameter compared to the second basket end (122).

Embodiment 16B: The device (100) of any one of embodiments 1B-15B, wherein the cells (123) are closed cells.

Embodiment 17B: The device (100) of any one of embodiments 1B-16B, wherein the cells (123) are quadrilateral in shape.

Embodiment 18B: The device (100) of any one of embodiments 1B-17B, wherein the cells (123) are rhombus in shape.

Embodiment 19B: The device (100) of any one of embodiments 1B-18B, wherein the struts (124) comprise surface heterogeneity.

Embodiment 20B: The device (100) of any one of embodiments 1B-19B, wherein the surface heterogeneity is on an inner surface of the struts (124).

Embodiment 21B: The device (100) of any one of embodiments 1B-19B, wherein the surface heterogeneity is on a lateral surface of the struts (124).

Embodiment 22B: The device (100) of embodiment 20B or embodiment 21B, wherein the surface heterogeneity comprises grooves, protrusions, or a combination thereof.

Embodiment 23B: The device (100) of any one of embodiments 1B-22B, wherein the plurality of cells (123) defined by struts (124) exert an outward radial force.

Embodiment 24B: The device (100) of any one of embodiments 1B-23B, wherein the plurality of cells (123) defined by struts (124) allow the embolus to ingress into the capturing basket (120).

Embodiment 25B: The device (100) of any one of embodiments 1B-24B, wherein the capturing basket (120) comprises at least six body markers (125).

Embodiment 26B: The device (100) of any one of embodiments 1B-25B, wherein the capturing basket (120) comprises at least eight body markers (125).

Embodiment 27B: The device (100) of any one of embodiments 1B-26B, wherein the body markers (125) are distributed equally between two portions of the capturing basket (120) created by a transverse plane.

Embodiment 28B: The device (100) of embodiment 27B, wherein the two portions of the capturing basket (120) comprise a distal portion and a proximal portion.

Embodiment 29B: The device (100) of embodiment 28B, where the body markers (125) are evenly distributed around the distal portion and/or the proximal portion of the capturing basket (120).

Embodiment 30B: The device (100) of embodiment 28B or embodiment 29B, wherein the body markers (125) in the distal portion and/or the proximal portion of the capturing basket (120) are 120° apart from each other.

Embodiment 31B: The device (100) of any one of embodiments 1B-30B, wherein the body markers (125) are disposed on the struts (124) of the capturing basket (120).

Embodiment 32B: The device (100) of embodiment 31B, wherein the body markers (125) are aligned with the struts (124) of the capturing basket (120).

Embodiment 33B: The device (100) of embodiment 31B, wherein the body markers (125) are protruded from the struts (124) of the capturing basket (120).

Embodiment 34B: The device (100) of any one of embodiments 1B-33B, wherein the body markers (125) are radiopaque markers.

Embodiment 35B: The device (100) of any one of embodiments 1B-34B, wherein the capturing basket (120) is deployable on a side of a clot in a blood vessel.

Embodiment 36B: The device (100) of any one of embodiments 1B-35B, wherein the capturing basket (120) is configured to rotate.

Embodiment 37B: The device (100) of any one of embodiments 1B-36B, wherein the capturing basket (120) rotates at low revolutions per minute (rpm).

Embodiment 38B: The device (100) of any one of embodiments 1B-37B, wherein the capturing basket (120) rotates at 2 to 10 rpm.

Embodiment 39B: The device (100) of any one of embodiments 1B-38B, wherein rotating the capturing basket (120) enables controlled shearing of the embolus.

Embodiment 40B: The device (100) of any one of embodiments 1B-39B, wherein rotating the capturing basket (120) dislodges the embolus from a vessel wall.

Embodiment 41B: The device (100) of any one of embodiments 1B-40B, wherein the capturing basket (120) is configured to retrieve embolus from two vessels at the same time.

Embodiment 42B: The device of any one of embodiments 1B-41B, wherein the delivery shaft (110) is braided.

Embodiment 43B: The device of any one of embodiments 1B-42B, wherein the delivery shaft (110) is hollow.

Embodiment 44B: The device of any one of embodiments 1B-43B, wherein the delivery shaft (110) is able to withstand torque.

Embodiment 45B: The device (100) of embodiment 44B, wherein the delivery shaft (110) is configured to rotate.

Embodiment 46B: The device (100) of embodiment 45B, wherein the delivery shaft (110) is hand rotated.

Embodiment 47B: The device (100) of embodiment 45B or embodiment 46B, wherein the delivery shaft (110) rotates at low revolutions per minute (rpm).

Embodiment 48B: The device (100) of embodiment 47B, wherein the delivery shaft (110) rotates at 2 to 10 rpm.

Embodiment 49B: The device (100) of any one of embodiments 44B-48B, wherein when the delivery shaft (110) is rotated torque is transferred from the delivery shaft (110) to the capturing basket (120), such that the capturing basket (120) is also rotated.

Embodiment 50B: The device of any one of embodiments 1B-49B further comprising a first end marker (126) and a second end marker (127).

Embodiment 51B: The device (100) of embodiment 50B, wherein the first end marker (126) is disposed at the first basket end (121) and the second end marker (127) is disposed at the second basket end (122).

Embodiment 52B: The device of embodiments 50B or embodiment 51B, wherein the first end marker (126) and the second end maker (127) are radiopaque markers.

Embodiment 53B: The device (100) of any one of embodiments 1B-52B, further comprising a delivery sheath (170).

Embodiment 54B: The device (100) of any one of embodiments 1B-53B, further comprising a delivery catheter (180).

Embodiment 55B: The device (100) of any one of embodiments 1B-54B, wherein the device is rotatable.

Embodiment 56B: The device (100) of embodiment 55B, wherein the device is rotated at 2-10 rpm.

Embodiment 57B: The device (100) of embodiment 55B or embodiment 56B, wherein rotating the device allows for controlled shearing of the clot.

Embodiment 58B: The device (100) of embodiment 55B or embodiment 56B, wherein rotating the device allows for the capturing basket (120) to dislodge the embolus from the vessel wall.

Embodiment 59B: The device (100) of any of embodiments 1B-58B, wherein the capturing basket (120) is configured to be retrieved by a distal opening of a catheter after the clot ingresses into the capturing basket (120).

Embodiments Set C

Embodiment 1C: A method of capturing a clot, the method comprising: (a) deploying a clot retrieval device (100) according to Embodiment Set B; and (b) expanding the capturing basket (120) on a side of the clot, between a vessel wall and the clot; wherein expanding the capturing basket (120) of the clot retrieval device (100) allows for the clot to ingress laterally into the capturing basket (120) of the clot retrieval device (100), thus capturing the clot.

Embodiment 2C: A method of retaining a clot in a clot retrieval device (100) as the clot retrieval device (100) is being pulled towards a catheter, the method comprising: (a) capturing the clot in a clot retrieval device (100) according to Embodiment Set B; and (b) visualizing and monitoring a distance between the body markers (125) on a portion of the capturing basket (120), wherein when the distance of the body markers (125) on the portion of the capturing basket (120) are stationary, the clot is retained in the capturing basket (120), and when the distance of the body markers (125), the portion of the capturing basket (120) changes the clot is escaping.

Embodiment 3C: A method of capturing and retaining a clot, the method comprising: (a) deploying a clot retrieval device (100) according to Embodiment Set B on a side of the clot; (b) expanding the capturing basket (120) on a side of the clot, between a vessel wall and the clot; wherein expanding the capturing basket (120) of the clot retrieval device (100) allows for the clot to ingress laterally into the capturing basket (120) of the clot retrieval device (100), thus capturing the clot; and (c) visualizing and monitoring a distance between the body markers (125) on a portion of the capturing basket (120) wherein when the distance of the body markers (125) on the portion of the capturing basket (120) is stationary, the clot is retained in the capturing basket (120), and when the distance of the body markers (125), the portion of the capturing basket (120) changes the clot is escaping.

Embodiment 4C: The method of embodiment 2C or embodiment 3C, wherein the distance of the body markers (125) on the portion of the capturing basket (120) increases.

Embodiment 5C: The method of embodiment 2C or embodiment 3C, wherein the distance of the body markers (125) on the portion of the capturing basket (120) decreases.

Embodiment 6C: The method of any one of embodiments 1C-5C, wherein the clot comprises an embolus.

Embodiment 7C: A method of indirectly visualizing a captured clot, comprising capturing the embolism with a capturing basket (120) according to Embodiment Set A and monitoring a distance between the body markers (125) on a portion of the capturing basket (120); wherein when the distance of the body markers (125) on the portion of the capturing basket (120) are stationary, the clot is captured and retained in the capturing basket (120), and when the distance of the body markers (125) the portion of the capturing basket (120) changes the clot lost from the capturing basket (120).

Embodiment 8C: The method of embodiment 7C, wherein the distance of the body markers (125) on the portion of the capturing basket (120) increases.

Embodiment 9C: The method of embodiment 7C, wherein the distance of the body markers (125) on the lateral side of the capturing basket (120) decreases.

Embodiment 10C: The method of any one of embodiments 7C-9C, wherein the clot comprises an embolus.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A clot retrieval device (100) comprising:
   a) a delivery shaft (110) having a distal delivery shaft end (111);
   b) a capturing basket (120) coupled to the distal delivery shaft end (111), wherein the capturing basket (120) comprises a first basket end (121), a second basket end (122), a plurality of cells (123) defined by struts (124), the struts (124) having strut ends that are connected to the first basket end (121) and the second basket end (122), and at least four body markers (125) disposed on the capturing basket (120); and
   c) a support component (150) coupled to the distal delivery shaft end (111) and disposed within the capturing basket (120), wherein the support component (150) comprises:
      i) a first support portion (130) comprising a first end (131), a second end (132), and a first lumen (133), wherein the first end (131) and the second end (132) of the first support portion (130) are disposed within the basket (120); and
      ii) a second support portion (140) comprising a first end (141), a second end (142), and a second lumen (143), wherein the first (141) and the second end (142) of the second support portion (140) are disposed within the basket (120).

2. The device (100) of claim 1, wherein the capturing basket comprises a diameter of 10 mm to 14 mm.

3. The device (100) of claim 2, wherein the diameter of the capturing basket (120) is tapered between the first basket end (121) and the second basket end (122), such that the first basket end (121) comprises a larger diameter compared to the second basket end (122).

4. The device (100) of claim 1, wherein the cells (123) are closed cells.

5. The device (100) of claim 4, wherein the cells (123) are quadrilateral in shape.

6. The device (100) of claim 1, wherein the struts (124) comprise surface heterogeneity.

7. The device (100) of claim 6, wherein the surface heterogeneity is on an inner surface of the struts (124), a lateral surface of the struts (124), or a combination thereof.

8. The device (100) of claim 7, wherein the surface heterogeneity comprises grooves, protrusions, or a combination thereof.

9. The device (100) of claim 1, wherein the capturing basket (120) further comprises at least six body markers (125).

10. The device (100) of claim 9, wherein the body markers (125) are distributed equally between two portions of the capturing basket (120) created by a transverse plane, wherein the two portions of the capturing basket (120) comprise a distal portion and a proximal portion.

11. The device (100) of claim 10, where the body markers (125) are evenly distributed 120° apart from each other around the distal portion and/or the proximal portion of the capturing basket (120).

12. The device (100) of claim 1, wherein the body markers (125) are disposed on the struts (124) of the capturing basket (120).

13. The device (100) of claim 12, wherein the body markers (125) are aligned with the struts (124) of the capturing basket (120).

14. The device (100) of claim 13, wherein the body markers (125) are radiopaque markers.

15. The device of claim 1 further comprising a first end marker (126) and a second end marker (127), wherein the first end marker (126) is disposed at the first basket end (121) and the second end marker (127) is disposed at the second basket end (122).

16. The device of claim 15, wherein the first end marker (126) and the second end maker (127) are radiopaque markers.

17. The device (100) of claim 1, wherein the device is rotatable.

18. The device (100) of claim 17, wherein the device is rotated at 2-10 rpm.

19. The device (100) of claim 17, wherein when the delivery shaft (110) of the clot retrieval device (100) is rotated torque is transferred through the delivery shaft (110) to the capturing basket (120), such that the capturing basket (120) is also rotated.

20. The device (100) of claim 19, wherein rotating the device allows for controlled shearing of the clot and dislodging the embolus from the vessel wall.

* * * * *